United States Patent
Little et al.

(10) Patent No.: US 7,232,688 B2
(45) Date of Patent: Jun. 19, 2007

(54) SYSTEMS AND METHODS FOR PREPARING AND ANALYZING LOW VOLUME ANALYTE ARRAY ELEMENTS

(75) Inventors: Daniel P. Little, Boston, MA (US); Maryanne J. O'Donnell-Maloney, Boston, MA (US); Charles R. Cantor, Boston, MA (US); Hubert Köster, La Jolla, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 09/364,774

(22) Filed: Jul. 30, 1999

(65) Prior Publication Data

US 2003/0096426 A1 May 22, 2003

Related U.S. Application Data

(62) Division of application No. 08/786,988, filed on Jan. 23, 1997.

(51) Int. Cl.
*G01N 24/00* (2006.01)
*G01N 1/10* (2006.01)
*B01D 59/44* (2006.01)

(52) U.S. Cl. .................. 436/173; 436/180; 250/287; 250/425

(58) Field of Classification Search ............... 250/288, 250/423 R, 442.11; 436/47, 173, 18; 422/104
See application file for complete search history.

(56) References Cited

U.S. PATENT DOCUMENTS

| | | | |
|---|---|---|---|
| 3,776,700 A | 12/1973 | Gallant | 23/259 |
| 4,740,692 A | 4/1988 | Yamamoto et al. | 250/282 |
| 4,952,518 A | 8/1990 | Johnson et al. | 436/518 |
| 5,175,209 A | 12/1992 | Beattie et al. | 525/54.11 |

(Continued)

FOREIGN PATENT DOCUMENTS

| | | | |
|---|---|---|---|
| DE | WO-9803257 A | * | 1/1998 |
| DE | 19731479 | | 8/1998 |
| EP | 0396116 | | 11/1990 |

(Continued)

OTHER PUBLICATIONS

Li et al. "Analysis of Single Mammalian Cell Lysates by Mass Spectrometry", J. Am. Chem. Soc., 1996, 118, pp. 11662–11663.
Beattie et al., "Synthesis and use of oligonucleotide libraries", Chem. Abst., 123:1172 (1995).
Lyttle et al., "Versatile Linker Chemistry for Synthesis of 3'-Modified DNA", Chem. Abst., 128(18):314 (1997).

(Continued)

*Primary Examiner*—Yelena G. Gakh
(74) *Attorney, Agent, or Firm*—Grant Anderson LLP

(57) ABSTRACT

Methods for dispensing tools that can be employed to generate multi-element arrays of sample material on a substrate surface. The resulting substrates are also provided. The substrates surfaces can be flat or geometrically altered to include wells of receiving material. The tool can dispense a spot of fluid to a substrate surface by spraying the fluid from the pin, contacting the substrate surface or forming a drop that touches against the substrate surface. The tool can form an array of sample material by dispensing sample material in a series of steps, while moving the pin to different locations above the substrate surface to form the sample array. The prepared sample arrays are passed to a plate assembly that disposes the sample arrays for analysis by mass spectrometry. To this end, a mass spectrometer is provided that generates a set of spectra signals that are indicative of the composition of the sample material under analysis.

31 Claims, 9 Drawing Sheets

U.S. PATENT DOCUMENTS

| | | | | |
|---|---|---|---|---|
| 5,288,644 | A | * 2/1994 | Beavis et al. | 436/94 |
| 5,350,676 | A | * 9/1994 | Oberhardt et al. | 435/13 |
| 5,399,501 | A | 3/1995 | Pope et al. | 436/532 |
| 5,498,545 | A | 3/1996 | Vestal | 436/47 |
| 5,506,348 | A | 4/1996 | Pieles | |
| 5,512,295 | A | 4/1996 | Kornberg et al. | 424/450 |
| 5,514,548 | A | 5/1996 | Krebber et al. | 435/6 |
| 5,547,835 | A | * 8/1996 | Koster | 435/6 |
| 5,580,434 | A | 12/1996 | Robotti et al. | 204/451 |
| 5,609,907 | A | 3/1997 | Natan | 427/2.12 |
| 5,643,800 | A | * 7/1997 | Tarantino et al. | 436/518 |
| 5,663,242 | A | 9/1997 | Ghosh et al. | 525/329.4 |
| 5,700,642 | A | * 12/1997 | Monforte et al. | 435/6 |
| 5,716,825 | A | 2/1998 | Hancock et al. | 435/286.5 |
| 5,742,049 | A | 4/1998 | Holle et al. | |
| 5,743,960 | A | 4/1998 | Tisone | 118/683 |
| 5,770,272 | A | 6/1998 | Biemann | |
| 5,770,860 | A | 6/1998 | Franzen | 250/288 |
| 5,777,324 | A | * 7/1998 | Hillenkamp | 250/288 |
| 5,812,272 | A | 9/1998 | King et al. | 356/445 |
| 5,828,063 | A | 10/1998 | Koster et al. | 250/288 |
| 5,854,486 | A | 12/1998 | Dreyfus | |
| 5,864,137 | A | 1/1999 | Becker et al. | 250/287 |
| 5,872,010 | A | 2/1999 | Karger et al. | 436/173 |
| 5,900,481 | A | * 5/1999 | Lough et al. | 536/55.3 |
| 5,925,520 | A | 7/1999 | Tully et al. | 435/6 |
| 5,927,547 | A | 7/1999 | Papen et al. | 222/57 |
| 5,965,363 | A | 10/1999 | Monforte et al. | 435/6 |
| 5,969,350 | A | * 10/1999 | Kerley et al. | 250/287 |
| 5,981,185 | A | 11/1999 | Matson et al. | 435/6 |
| 5,985,356 | A | 11/1999 | Schultz et al. | 427/8 |
| 6,024,925 | A | 2/2000 | Little et al. | 422/100 |
| 6,040,193 | A | 3/2000 | Winkler et al. | 436/180 |
| 6,051,378 | A | 4/2000 | Monforte et al. | 435/6 |
| 6,079,283 | A | 6/2000 | Papen et al. | 73/864.11 |
| 6,083,762 | A | 7/2000 | Papen et al. | 436/180 |
| 6,090,558 | A | 7/2000 | Butler et al. | 435/6 |
| 6,104,028 | A | 8/2000 | Hunter et al. | 250/288 |
| 6,110,426 | A | 8/2000 | Shalon et al. | 422/68.1 |
| 6,121,048 | A | 9/2000 | Zaffaroni et al. | 436/45 |
| 6,136,269 | A | 10/2000 | Winkler et al. | 422/61 |
| 6,194,144 | B1 | 2/2001 | Köster | 435/6 |
| 6,197,498 | B1 | 3/2001 | Köster | 435/6 |
| 6,207,370 | B1 | 3/2001 | Little et al. | 435/6 |
| 6,221,601 | B1 | 4/2001 | Köster et al. | 435/6 |
| 6,221,605 | B1 | 4/2001 | Köster | 435/6 |
| 6,225,061 | B1 | 5/2001 | Becker et al. | 435/6 |
| 6,225,450 | B1 | 5/2001 | Köster | 536/22.1 |
| 6,235,478 | B1 | 5/2001 | Köster | 435/6 |
| 6,238,871 | B1 | 5/2001 | Köster | 435/6 |
| 6,258,538 | B1 | 7/2001 | Köster et al. | 435/6 |
| 6,265,716 | B1 | 7/2001 | Hunter et al. | 250/288 |
| 6,268,131 | B1 | 7/2001 | Kang et al. | 435/6 |
| 6,268,144 | B1 | 7/2001 | Köster | 435/6 |
| 6,277,573 | B1 | 8/2001 | Koster | 435/6 |
| 6,287,872 | B1 | 9/2001 | Schurenberg et al. | |
| 6,300,076 | B1 | 10/2001 | Köster | 435/6 |
| 6,303,309 | B1 | 10/2001 | Jurinke et al. | 435/6 |
| 6,322,970 | B1 | 11/2001 | Little et al. | 435/6 |
| 6,342,396 | B1 | 1/2002 | Perrin et al. | 436/518 |
| 6,376,044 | B1 | 4/2002 | Jarrell et al. | 428/141 |
| 6,387,628 | B1 | 5/2002 | Little et al. | 435/6 |
| 6,428,955 | B1 | 8/2002 | Köster et al. | 435/6 |
| 6,485,913 | B1 | 11/2002 | Becker et al. | 435/6 |
| 6,500,621 | B2 | 12/2002 | Köster | 435/6 |
| 6,558,902 | B1 | 5/2003 | Hillenkamp | 435/6 |
| 6,566,055 | B1 | 5/2003 | Monforte et al. | 435/6 |
| 6,569,385 | B1 | 5/2003 | Little et al. | 422/100 |
| 6,589,485 | B2 | 7/2003 | Köster | 422/104 |
| 6,602,662 | B1 | 8/2003 | Köster et al. | 435/6 |
| 6,635,452 | B1 | 10/2003 | Monforte et al. | 435/91.1 |
| 6,670,609 | B2 | 12/2003 | Franzen et al. | |
| 2002/0109085 | A1 | 8/2002 | Hillenkamp et al. | |
| 2003/0022225 | A1 | 1/2003 | Monforte et al. | |
| 2003/0113745 | A1 | 6/2003 | Monforte et al. | |
| 2003/0228594 | A1 | 12/2003 | Koster et al | |

FOREIGN PATENT DOCUMENTS

| | | |
|---|---|---|
| EP | 0543550 | 5/1993 |
| EP | 1262564 | 1/1994 |
| EP | 1271609 | 9/1997 |
| EP | 1164203 | 11/1997 |
| GB | 2233654 | 1/1991 |
| GB | 2312782 | 11/1997 |
| GB | 2332273 | 6/1999 |
| JP | 2215399 | 8/1990 |
| JP | A-8-233710 | 9/1996 |
| WO | 8805074 | 7/1988 |
| WO | 8912624 | 12/1989 |
| WO | 9314108 | 7/1993 |
| WO | 9403774 | 2/1994 |
| WO | 9427719 | 12/1994 |
| WO | 9511755 | 5/1995 |
| WO | 9525116 | 9/1995 |
| WO | 9525175 | 9/1995 |
| WO | 9535505 | 12/1995 |
| WO | 9619587 | 6/1996 |
| WO | 9803257 | 1/1998 |
| WO | 9805965 | 2/1998 |
| WO | 9822541 | 5/1998 |
| WO | 9834116 | 8/1998 |
| WO | 9839481 | 9/1998 |

OTHER PUBLICATIONS

Asseline et al. "New Solid–Phase For Automated Synthesis of Oligonucleotides Containing An Amino–Alkyl Linker at Their 3'–End," *Tetrahedron Letters 31(1)*: 81–84 (1990).

Beattie et al., "123:112593k Synthesis and use of oligonucleotide libraries," *Chemical Abstracts 123*: 1172 (1995).

Bonfils, E. and N.T. Thuong. "Solid Phase Synthesis of 5', 3'Bifunctional Oligodeoxyribonucleotides Bearing a Masked Thiol Group at the 3'–End," *Tetrahedron Letters 32(26)*: 3053–3056 (1991).

Day et al., "Immobilization of polynucleotides on magnetic particles," *Biochem. J. 278*: 735–740 (1991).

Debitsudo, A. "121:109581h Preparation of oligonucleotide monolayer," *Chemical Abstracts 121*: 1163:1163 (1994).

Debitsudo, A. "121:83891g Preparation of nucleotide thioalkyl esters and monomolecular membrane," *Chemical Abstracts 121*: 1166 (1994).

Debitsudo, A. "122:291447q Organic super–thin fim of oligonucleotide derivative and method for its preparation," *Chemical Abstracts 122*: 1100 (1995).

Derwent No. 011716230, WPI Acc. No. 1998–133140/199813 for PCT Patent Application WO9805965 A1, "Identification of characteristics of eukaryotic cells—after covalent immobilisation on solid support,".

Derwent No. 011999582, WPI Acc. No. 1998–416492/199836 for PCT Patent Application WO9834116 A1, "Isolation and determination of analyte—by capture on specific binding particles and concentration of these on second, limited binding surface before detection, used e.g. for detecting RNA,".

Derwent No. 012012061, WPI Acc. No. 1998–428971/ 199837 for German Patent Application DE19731479 A, "Device for analysis of target chemicals has light emitting array—with chemical binder elements attached to array to capture target chemicals which change emitted light pattern accordingly,".

Emmett, M.R. and R.M. Caprioli. "Micro–Electrospray Mass Spectrometry: Ultra–High–Sensitivity Analysis of Peptides and Proteins," *J. Am. Soc. Mass Spectrometry* 5: 605–613 (1994).

Hofstadler et al. "Capillary Electrophoresis—Electrospray Ionization Fourier Transform Ion Cyclotron Resonance Mass Spectrometry for Direct Analysis of Cellular Proteins," *Anal. Chem.* 67: 1477–1480 (1995).

Jespersen et al. "Attomole Detection of Proteins by Matrix–assisted Laser Desorption/Ionization Mass Spectrometry with the Use of Picolitre Vials," *Rapid Communications in Mass Spectrometry* 8(8): 581–584 (1994).

Li et al. "Analysis of Single Mammalain Cell Lysates by Mass Spectrometry," *J. Am. Chem. Soc.* 118: 11662–11663 (1996).

Lyttle, M.H. "126:235533k Versatile Linker Chemistry for Synthesis of 3'–Modified DNA," *Chemical Abstracts* 126(18): 314 (1997).

Solouki et al. "Attomole Biomolecule Mass Analysis by MAtrix–Assisted Laser Desorption/Ionization Fourier Transform Ion Cyclotron Resonance," *Anal. Chem.* 67:4139–4144 (1995).

Wilm et al. "Electrospray and Taylor–Cone theory, Dole's beam of macromolecules at last," *International Journal of Mass Spectrometry and Ion Processes* 136: 167–180 (1994).

Valaskovic et al. "Attomole Protein Characterization by Capillary Electrophoresis—Mass Spectrometry," *Science* 273: 1199–1202 (1996).

Valaskovic et al. "Attomole–Sensitivity Electrospray Source for Large–Molecule Mass Spectrometry," *Anal. Chem.* 67: 3802–3805 (1995).

Wahl et al. "Use of small–diameter capillaries for increasing peptide and protein detection sensitivity in capillary electrophoresis–mass spectrometry," *Electrophoresis* 14: 448–457 (1993).

Zhang et al. "Micro–preparation Proceduire for High–sensitivity Matrix–assisted Laser Desorption Ionization Mass Spectrometry," *Journal of Mass Spectrometry* 30: 1768–1771 (1995).

Lee, et al., Direct Measurement of the Forces Between Complementary Strands of DNA, Science, vol. 266, Nov. 4, 1994, 771–773.

Vorm, et al, Improved Mass Accuracy in Matrix–Assisted Laser Desorption/Ionization Time–Of–Flight Mass Spectrometry of Peptides. Journal of The American Society For Mass Spectrometry, Nov, 1994, V5(N11): 955–958.

Schober, et al., Accurate High–Speed Liquid Handling of Very Small Biological Samples, Biotechniques, (1993) 15(2):324–329.

Certified English language translation of WO98/03257, "Solid supports for analytical measurement methods, their production and their use," cited at item AJ.

Derwent #011716230, WPI Acc. No. 1998/199813, for PCT Patent Application WO 9805965 A, "Identification of characteristics of eukaryotic cells –after covalent immobilisation on solid support," cited at Item AK.

Derwent #01201061 , WPI Acc. No. 1998–428971/199837, for German Application No. DE 19731479 A1, "Device for analysis of target chemicals has light emitting array –with chemical binder elements attached to array to capture target chemicals which change emitted light pattern accordingly," cited at item AB.

Derwent #002061834, WPI Acc. No. 90–302767, for Japenese Application No. JP 2215399, "Method for detecting DNA –includes de–naturing to single strand, combining with DNA primer having corresp. base sequence forming replicator etc," cited at Item AC.

Manoharan et al., "A 2'–O–thiol Tether in the Ribose Moiety of Nucleic Acids for Conjugation Chemistry", *Gene,* 149: 147–156 (1994).

O'Donnel–Maloney et al., "Microfabrication and Array Technologies for DNA Sequencing and Diagnostics", *Genetic Analysis Biomolecular Engineering,* 13:161–157 (1996).

Pon et al., "Derivatization of Controlled Pore Glass Beads for Solid Phase Oligonucleotide Synthesis", *Bio Technique,* 6(8): 768–770, 773–775 (1988).

Zhange et al., "Micro–preparation Procedure For High–sensitivity Matrix–assisted Laser Desorption Ionization Mass Spectrometry", JMS, vol. 30, 1768–1771 (Sept. 1995).*

Office Action mailed on Mar. 18, 2003 for Copending U.S. Appl. No. 08/786,988.*

Brummel et al. "Evaluation of mass spectrometric methods applicable to the direct analysis of non–peptide bead–bound combinatorial libraries", Anal. Chem., 1996, v. 68, pp. 237–242.*

Dai, Yugin, et al., Two–Layer Sample Preparation: A Method for MALDI–MS Analysis of Complex Peptide and Protein Mixtures, Analytical. Chemistry, (1999), 1087–1097, 71(5), American Chemical Society.

Nicola, Anthony J., et al., Application of the Fast–evaporation Sample Preparation Method for improving Quantification of Angiotensin II by Matrix–assisted Laser Desorption/Ionization, Rapid Communications in Mass Spectrometry, (1995), 1164–1171, 9, John Wiley & Sons, Ltd.

Vorm, Ole, et al., Improved Resolution and Very High Sensitivity in MALDI TOF of Matrix Surface Made by Fast Evaporation, Analytical Chemistry, (1994), 3281–3287, 66(19), American Chemical Society.

Vorm, Ole, et al, Improved Mass Accuracy in Matrix–Assisted Laser Desorption/Ionization Time–of–Flight Mass Spectrometry of Peptides, J. Am. Soc. Mass Spectrom, (1994), 955–958, 6, American Society for Mass Spectrometry.

Fast Evaporation, http://www.chemistry.wustl.edu/–msf/damon/samp_fast$_{13}$ evap.html, pp. 1–2, Sample Preparation – Fast Evaporation.

Sample Preparation –References, pp. 1–3 http://www.chemistry.wustl.edu/~msf/damon/samp_prep_references.html.

On–Probe Decontamination for MALDI Samples, pp. 1–2, http://www.chemistry.msu.edu/faculty/bruening/on-probepurification.htm, Matrix.

M.C. Fitzgerald et al., "The promise of matrix–assisted laser desorption–ionization (MALDI) mass spectrometry," Annu. Rev. Biophys. Biomol. Struct. 24: 117–140 (1995).

English language abstract from Japanese Patent Office for JP–A–8–233710.

* cited by examiner

| k1 6968 Da 170 RP | k2 6968 Da 100 RP | k3 6988 Da 90 RP | k4 6977 Da 100 RP | k5 6971 Da 170 RP | k6 6968 Da 110 RP | k7 6972 Da 160 RP | k8 6978 Da 110 RP | k9 6952 Da 250 RP | k10 6965 Da 300 RP |
|---|---|---|---|---|---|---|---|---|---|
| l1 6965 Da 130 RP | l2 6989 Da 140 RP | l3 6982 Da 210 RP | l4 6996 Da 50 RP | l5 6982 Da 160 RP | l6 6968 Da 180 RP | l7 6984 Da 130 RP | l8 6968 Da 200 RP | l9 6996 Da 80 RP | l10 6968 Da 100 RP |
| m1 6966 Da 190 RP | m2 6979 Da 120 RP | m3 6975 Da 120 RP | m4 6968 Da 190 RP | m5 6976 Da 110 RP | m6 6986 Da 120 RP | m7 6973 Da 160 RP | m8 6978 Da 160 RP | m9 6975 Da 230 RP | m10 6955 Da 250 RP |
| n1 6961 Da 340 RP | n2 6971 Da 180 RP | n3 6970 Da 150 RP | n4 6960 Da 300 RP | n5 6985 Da 120 RP | n6 6953 Da 210 RP | n7 6971 Da 140 RP | n8 6962 Da 160 RP | n9 6957 Da 150 RP | n10 6960 Da 160 RP |
| o1 6965 Da 140 RP | o2 6960 Da 230 RP | o3 6976 Da 200 RP | o4 6953 Da 250 RP | o5 6983 Da 110 RP | o6 6967 Da 250 RP | o7 6970 Da 150 RP | o8 6973 Da 70 RP | o9 6953 Da 140 RP | o10 6952 Da 140 RP |
| p1 6976 Da 140 RP | p2 6981 Da 90 RP | p3 6972 Da 180 RP | p4 6969 Da 90 RP | p5 6984 Da 130 RP | p6 6968 Da 100 RP | p7 6958 Da 290 RP | p8 6981 Da 100 RP | p9 6978 Da 110 RP | p10 6965 Da 150 RP |
| q1 6976 Da 170 RP | q2 6985 Da 100 RP | q3 6990 Da 120 RP | q4 6989 Da 90 RP | q5 6984 Da 90 RP | q6 6969 Da 170 RP | q7 6979 Da 70 RP | q8 6968 Da 140 RP | q9 6973 Da 120 RP | q10 6950 Da 120 RP |
| r1 6966 Da 130 RP | r2 6960 Da 150 RP | r3 6969 Da 100 RP | r4 6964 Da 180 RP | r5 6966 Da 130 RP | r6 6970 Da 110 RP | r7 6972 Da 90 RP | r8 6939 Da 130 RP | r9 6951 Da 230 RP | r10 6965 Da 200 RP |
| s1 6963 Da 130 RP | s2 6953 Da 210 RP | s3 6970 Da 120 RP | s4 6971 Da 170 RP | s5 6957 Da 130 RP | s6 6956 Da 160 RP | s7 6966 Da 140 RP | s8 6975 Da 120 RP | s9 6951 Da 230 RP | s10 6969 Da 120 RP |
| t1 6974 Da 90 RP | t2 6958 Da 160 RP | t3 6959 Da 120 RP | t4 6952 Da 100 RP | t5 6959 Da 110 RP | t6 6954 Da 100 RP | t7 6950 Da 160 RP | t8 6974 Da 140 RP | t9 6967 Da 150 RP | t10 6950 Da 230 RP |

LASER POWER = 41000 FOR ALL SPECTRA.
EACH SPECTRUM THE SUM OF 10–30 SINGLE SHOTS.

FIG. 9

SYSTEMS AND METHODS FOR PREPARING AND ANALYZING LOW VOLUME ANALYTE ARRAY ELEMENTS

RELATED APPLICATIONS

This application is a divisional of U.S. application Ser. No. 08/786,988 to Little et al., entitled SYSTEMS AND METHODS FOR PREPARING AND ANALYZING LOW VOLUME ANALYTE ARRAY ELEMENTS, filed Jan. 23, 1997. The subject matter of U.S. application Ser. No. 08/786,988 is incorporated herein in its entirety.

FIELD OF THE INVENTION

The invention relates to systems and methods for preparing a sample for analysis, and more specifically to systems and methods for dispensing low volumes of fluid material onto a substrate surface for generating an array of samples for diagnostic analysis.

BACKGROUND OF THE INVENTION

In recent years, developments in the field of life sciences have proceeded at a breathtaking rate. Universities, hospitals and newly formed companies have made groundbreaking scientific discoveries and advances that promise to reshape the fields of medicine, agriculture, and environmental science. However, the success of these efforts depends, in part, on the development of sophisticated laboratory tools that will automate and expedite the testing and analysis of biological samples. Only upon the development of such tools can the benefits of these recent scientific discoveries be achieved fully.

At the forefront of these efforts to develop better analytical tools is a push to expedite the analysis of complex biochemical structures. This is particularly true for human genomic DNA, which is comprised of at least about one hundred thousand genes located on twenty four chromosomes. Each gene codes for a specific protein, which fulfills a specific biochemical function within a living cell. Changes in a DNA sequence are known as mutations and can result in proteins with altered or in some cases even lost biochemical activities; this in turn can cause a genetic disease. More than 3,000 genetic diseases are currently known. In addition, growing evidence indicates that certain DNA sequences may predispose an individual to any of a number of genetic diseases, such as diabetes, arteriosclerosis, obesity, certain autoimmune diseases and cancer. Accordingly, the analysis of DNA is a difficult but worthy pursuit that promises to yield information fundamental to the treatment of many life threatening diseases.

Unfortunately, the analysis of DNA is made particularly cumbersome due to size and the fact that genomic DNA includes both coding and non-coding sequences (e.g., exons and introns). As such, traditional techniques for analyzing chemical structures, such as the manual pipeting of source material to create samples for analysis, are of little value. To address the scale of the necessary analysis, scientist have developed parallel processing protocols for DNA diagnostics.

For example, scientists have developed robotic devices that eliminate the need for manual pipeting and spotting by providing a robotic arm that carries at its proximal end a pin tool device that consists of a matrix of pin elements. The individual pins of the matrix are spaced apart from each other to allow each pin be dipped within a well of a microtiter plate. The robotic arm dips the pins into the wells of the microtiter plate thereby wetting each of the pin elements with sample material. The robotic arm then moves the pin tool device to a position above a target surface and lowers the pin tool to the surface contacting the pins against the target to form a matrix of spots thereon. Accordingly, the pin tool expedites the production of samples by dispensing sample material in parallel.

Although this pin tool technique works well to expedite the production of sample arrays, it suffers from several drawbacks. First during the spotting operation, the pin tool actually contacts the surface of the substrate. Since each pin tool requires a fine point to print a small spot size is printed onto the target, the continuous contact of the pin tool against the target surface will wear and deform the fine and delicate points of the pin tool. This leads to errors which reduce accuracy and productivity.

An alternative technique developed by scientists employs chemical attachment of sample material to the substrate surface. In one particular process, DNA is synthesized in situ on a substrate surface to produce a set of spatially distinct and diverse chemical products. Such techniques are essentially photolithographic in that they combine solid phase chemistry, photolabile protecting groups and photo activated lithography. Although these systems work well to generate arrays of sample material, they are chemically intensive, time consuming, and expensive.

It is further troubling that neither of the above techniques provide sufficient control over the volume of sample material that is dispensed onto the surface of the substrate. Consequently, error can arise from the failure of these techniques to provide sample arrays with well controlled and accurately reproduced sample volumes. In an attempt to circumvent this problem, the preparation process will often dispense generous amounts of reagent materials. Although this can ensure sufficient sample volumes, it is wasteful of sample materials, which are often expensive and of limited availability.

Even after the samples are prepared, scientists still must confront the need for sophisticated diagnostic methods to analyze the prepared samples. To this end, scientists employ several techniques for identifying materials such as DNA. For example, nucleic acid sequences can be identified by hybridization with a probe which is complementary to the sequence to be identified. Typically, the nucleic acid fragment is labeled with a sensitive reporter function that can be radioactive, fluorescent, or chemiluminescent. Although these techniques can work well, they do suffer from certain drawbacks. Radioactive labels can be hazardous and the signals they produce decay over time. Nonisotopic (e.g. fluorescent) labels suffer from a lack of sensitivity and fading of the signal with high intensity lasers are employed during the identification process. In addition, labeling is a laborious and time consuming error prone procedure.

Consequently, the process of preparing and analyzing arrays of a biochemical sample material is complex and error prone.

SUMMARY OF THE INVENTION

Accordingly, it is an object of the invention to provide improved systems and methods for preparing arrays of sample material.

It is a further object of the invention to provide systems that allow for the rapid production of sample arrays.

It is yet another object of the invention to provide systems and methods for preparing arrays of sample material that are less expensive to employ and that conserve reagent materials.

It is a further object of the invention to provide systems and methods for preparing arrays of sample material that provide high reproducibility of the arrays generated.

Other objects of the invention will in part be obvious and in part be disclosed in the following.

In certain embodiments serial and parallel dispensing tools that can be employed to generate multi-element arrays of sample material on a substrate surface are provided. The substrates surfaces can be flat or geometrically altered to include wells of receiving material. In one embodiment, a tool that allows the parallel development of a sample array is provided. To this end, the tool can be understood as an assembly of vesicle elements, or pins, wherein each of the pins can include a narrow interior chamber suitable for holding nanoliter volumes of fluid. Each of the pins can fit inside a housing that itself has in interior chamber. The interior housing can be connected to a pressure source that will control the pressure within the interior housing chamber to regulate the flow of fluid through the interior chamber of the pins. This allows for the controlled dispensing of defined volumes of fluid from the vesicles. In an alternative embodiment, a tool that includes a jet assembly that can include a capillary pin having an interior chamber, and a transducer element mounted to the pin and capable of driving fluid through the interior chamber of the pin to eject fluid from the pin is provided. In this way, the tool can dispense a spot of fluid to a substrate surface by spraying the fluid from the pin. Alternatively, the transducer can cause a drop of fluid to extend from the capillary so that fluid can be passed to the substrate by contacting the drop to the surface of the substrate. Further, the tool can form an array of sample material by dispensing sample material in a series of steps, while moving the pin to different locations above the substrate surface to form the sample array. In a further embodiment, the system then passes the prepared sample arrays to a plate assembly that disposes the sample arrays for analysis by mass spectrometry. To this end, a mass spectrometer is provided that generates a set of spectra signal which can be understood as indicative of the composition of the sample material under analysis.

Methods for preparing an array of sample material on a surface of a substrate are provided. The methods according can include the steps of providing a vesicle having an interior chamber containing a fluid, disposing the vesicle adjacent to a first location on the surface of the substrate, controlling the vessel for delivering a nanoliter volume of a fluid at the first location of the surface of the substrate, and moving the vesicle to a set of positions adjacent to the surface substrate whereby fluid is dispensed at each location of the set of positions for forming an array of sample material.

Substrates employed during the processes can include flat surfaces for receiving the sample material as well as having the surfaces that include wells formed on the surface for defining locations for receiving the fluid that can be ejected from the chambers of the vesicles. The substrates can be silicon, metal, plastic, a membrane, polymeric material, a metal-grafted polymer, as well as a substrate that is functionalized chemically, functionalized with beads, functionalized with dendrite trees of captured material, or any combinations of the above or any similar suitable material for receiving the dispensed fluid.

It is understood that the methods provided herein can dispense both an analyte material well as a support material, such as a matrix material, that aids in the analysis of the analyte. To this end the methods provided herein can include the steps of depositing a matrix material onto the substance of the substrate. Further the methods can also include a step of waiting a predetermined period of time to allow a solvent of the matrix material to evaporate. Once the solvent of the matrix material has evaporated, the methods can include a step of ejecting a volume of analyte fluid into the evaporated matrix material to dissolve with the matrix material and to form a crystalline structure on the substrate surface. It is understood that this step of redissolving the matrix material with the analyte material aids in the analysis of the composition of the material during certain analytical processes, such as mass spectrometry.

In an alternative practice, the methods can include a step of dispensing a mixture that consists of the analyte material and the matrix material, as well as other material compositions. In this way the matrix and the analyte are delivered to the surface of the substrate as one volume of material. In a further step, the prepared arrays of sample material can be provided to a diagnostic tool for determining information that is representative of the composition of the sample material.

Once such diagnostic tool can include a mass spectrometer. The mass spectrometer can be a time of flight mass spectrometer, Fourier transform mass spectrometers or any other suitable type of mass spectrometer that allows the analysis of composition of the sample array.

In practicing the methods, the step of providing a vesicle having an interior chamber includes the step of providing a vesicle having a piezo electric element for causing fluid to move through the chamber. This method can also include the step of moving the vesicle by rasterizing the vesicle across the surface of the substrate, to form the array of sample material.

In an alternative embodiment, parallel processing protocols can be employed wherein the vesicle that is employed during the processing includes a vesicle assembly that has a plurality of vesicles arranged into a matrix for dispensing fluid to a first plurality of location on the substrate surface. In this way in a single operation, the method provides for forming a matrix of sample material on the substrate surface. In a further embodiment, offset printing can be employed to form a large matrix of sample material by employing multiple printing steps with the vesicle matrix. Other printing techniques can be employed by the in the methods provided herein without departing from the scope thereof.

In another embodiment of the methods provided herein, fluid can be dispensed to the surface of the substrate by contacting the vesicle against the surface of the substrate to spot the surface of the substrate with sample material. Alternatively, another non-contact printing approach wherein the processes of the invention cause a drop of fluid to be formed on at the distal tip of the vesicle is provided. It is the drop of fluid that is contacted against the surface of the substrate for delivering sampling material thereto. This provides for the controlled delivery for the known volume of fluid without resulting in the contacting of the vesicle against the surface of the substrate.

In a further practice of the invention, vesicles are provided having an interior chamber that is dimensionally adapted to allow filling of the chamber by capillary action.

In another aspect, the invention can be understood as a method for analyzing a material, that comprises the steps of providing a vesicle suitable for carrying a fluid having the material therein, disposing the vesicle adjacent to a first location of the surface of the substrate, controlling the vesicle to deliver a nanoliter volume of the fluid to provide a defined and controlled volume of fluid at the first location of the surface of the substrate, moving the vesicle to a second position adjacent to a second location on the surface on the substrate to dispense a defined and controlled volume of the material along an array of locations along the substrate surface, and performing mass spectrometry analysis of the material at each location of the array. This method can include the step of mixing a matrix material and an analyte material to form the fluid being delivered to the substrate surface. Alternatively, this embodiment can include the steps of filling a chamber contained within the vesicle with a matrix material and dispensing the matrix material to the array of locations. Subsequently, analyte can be dispensed.

The step of performing mass spectrometry can include the step of performing a matrix assisted laser desorption ionization mass spectrometry, as well as time of flight mass spectrometry, or a fourier transform spectrometry. In another aspect, an apparatus for forming an array of a sample material on a surface of a substrate is provided. Such apparatus includes a vesicle having a distal end suitable for carrying a fluid thereon, a movable arm having a distal portion mounted to the vesicle, a controller for moving the arm to dispose the vesicle adjacent to a first location on the surface on the substrate and for controlling the vesicle to provide a nanoliter volume of the fluid at the first location of the surface of the substrate, and a diagnostic tool for analyzing the material to generate a composition signal that is representative of the chemical composition of the material. In this apparatus the vesicle can comprise a solid shaft of material as well as a vesicle having an interior chamber suitable for carrying fluid as well as a chamber for carrying a fluid in a transducer element for ejecting fluid from that chamber. In another aspect, a substrate having a surface for carrying an array of a matrix material and formed according to a process comprising the steps of providing a vesicle suitable for transferring a fluid containing a matrix material, disposing the vesicle adjacent to a first location on the surface on the substrate, controlling the vesicle of the volume fluid to the first location of the surface of the substrate, and moving a vesicle to a set of positions adjacent the surface of the substrate and delivering fluid at each of these locations to form an array of matrix material is provided. This substrate can be a flat silicon chip as well as any other suitable material, and can be pitted, include wells, and have wells that have rough interior surfaces.

BRIEF DESCRIPTION OF THE DRAWINGS

FIG. 9 depicts molecular weights determined for the sample material having spectra identified in FIG. 8.

DETAILED DESCRIPTION OF THE ILLUSTRATED EMBODIMENTS

Figure 1:
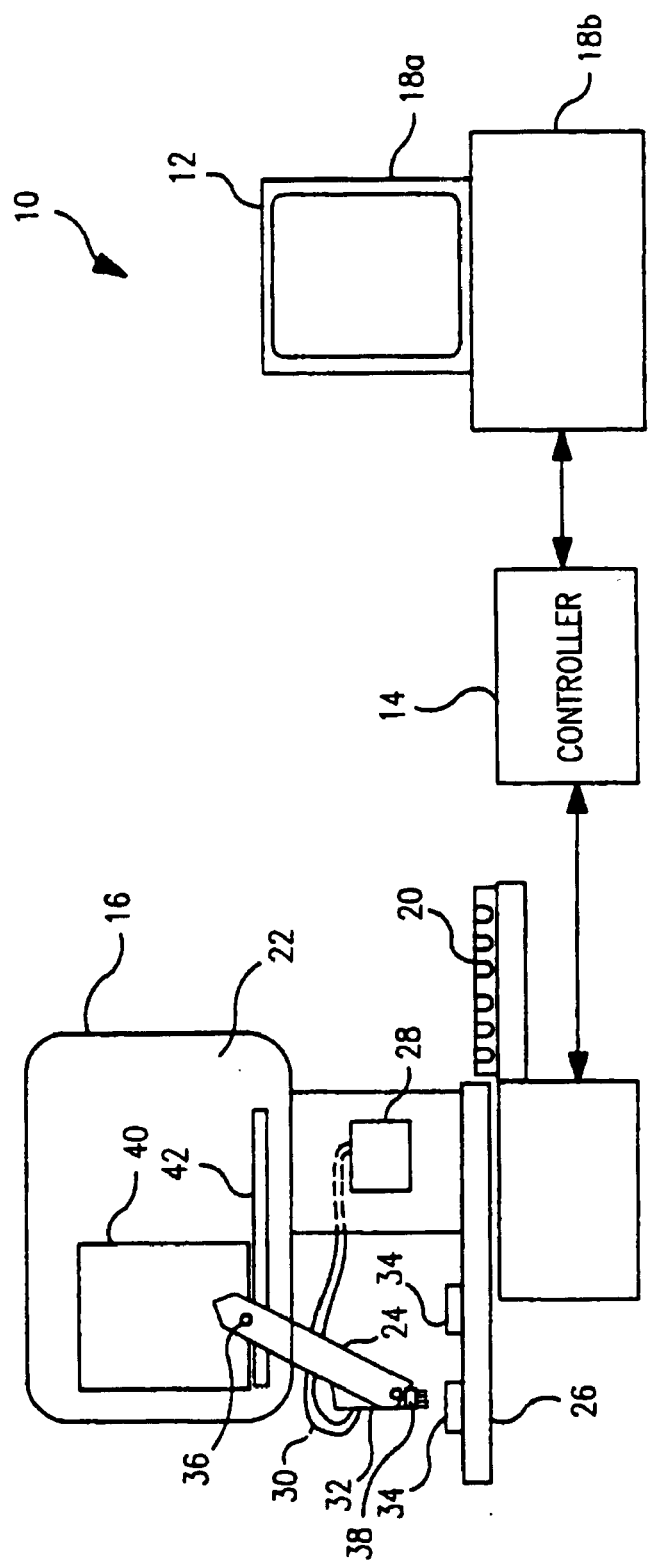
FIG. 1 illustrates one system provided herein for preparing arrays of a sample material for analysis.

FIG. 1 illustrates one system provided herein for preparing arrays of sample material for analysis by a diagnostic tool. FIG. 1 depicts a system 10 that includes a data processor 12, a motion controller 14, a robotic arm assembly 16, a monitor element 18A, a central processing unit 18B, a microliter plate of source material 20, a stage housing 22, a robotic arm 24, a stage 26, a pressure controller 28, a conduit 30, a mounting assembly 32, a pin assembly 38, and substrate elements 34. In the view shown by FIG. 1, it is also illustrated that the robotic assembly 16 can include a moveable mount element 40 and a horizontal slide groove 42. The robotic arm 24 can optionally pivot about a pin 36 to increase the travel range of the arm 24 so that arm 24 can dispose the pin assembly 38 above the source plate 20.

The data processor 12 depicted in FIG. 1 can be a conventional digital data processing system such as an IBM PC compatible computer system that is suitable for processing data and for executing program instructions that will provide information for controlling the movement and operation of the robotic assembly 16. It will be apparent to one skilled in the art that the data processor unit 12 can be any type of system suitable for processing a program of instruction signals that will operate the robotic assembly that is integrated into the robotic housing 16. Optionally the data processor 12 can be a micro-controlled assembly that is integrated into robotic housing 16. In further alternative embodiments, the system 10 need not be programmable and can be a singleboard computer having a firmware memory for storing instructions for operating the robotic assembly 16.

In the embodiment depicted in FIG. 1, there is a controller 14 that electronically couples between the data processor 12 and the robotic assembly 16. The depicted controller 14 is a motion controller that drives the motor elements of the robotic assembly 16 for positioning the robotic arm 24 at a selected location. Additionally, the controller 14 can provide instructions to the robotic assembly 16 to direct the pressure controller 28 to control the volume of fluid ejected from the individual pin elements of the depicted pin assembly 38. The design and construction of the depicted motion controller 14 follows from principles well known in the art of electrical engineering, and any controller element suitable for driving the robotic assembly 16 can be used.

The robotic assembly 16 depicted in FIG. 1 electronically couples to the controller 14. The depicted robotic assembly 16 is a gantry system that includes an XY table for moving the robotic arm about a XY plane, and further includes a Z axis actuator for moving the robotic arm orthogonally to that XY plane. The robotic assembly 16 depicted in FIG. 1 includes an arm 24 that mounts to the XY stage which moves the arm within a plane defined by the XY access. In the depicted embodiment, the XY table is mounted to the Z actuator to move the entire table along the Z axis orthogonal to the XY plane. In this way, the robotic assembly provides three degrees of freedom that allows the pin assembly 38 to be disposed to any location above the substrates 34 and the source plate 20 which are shown in FIG. 1 as sitting on the stage 26 mounted to the robotic assembly 16.

The depicted robotic assembly 16 follows from principles well known in the art of electrical engineering and is just one example of a robotic assembly suitable for moving a pin assembly to locations adjacent to a substrate and source plate such as the depicted substrate 34. accordingly, it will be apparent to one of skill in the art that alternative robotic systems can be employed.

FIG. 1 depicts an embodiment of a robotic assembly 16 that includes a pressure controller 28 that connects via a conduit 30 to the mount 32 that connects to the pin assembly 38. In this embodiment the mount 32 has an interior channel for fluidicly coupling the conduit 30 to the pin assembly 38. Accordingly, the pressure controller 28 is fluidicly coupled by the conduit 30 and the mount 32 to the pin assembly 38. In this way the controller 14 can send signals to the pressure controller 28 to control selectively a fluid pressure delivered to the pin assembly 38.

Figure 2:
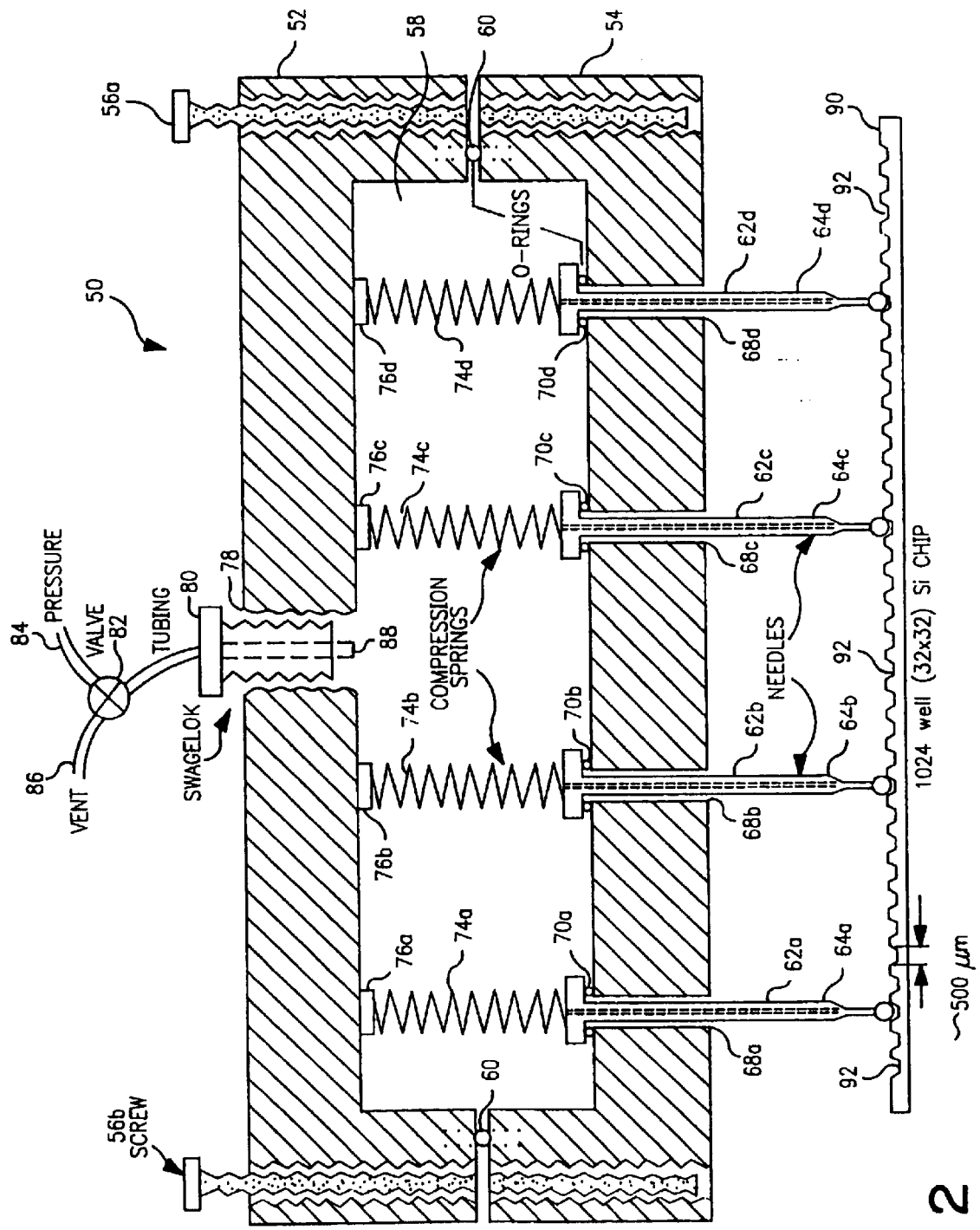
FIG. 2 illustrates a pin assembly suitable for use with the system depicted in FIG. 1 for implementing a parallel process of dispensing material to a surface of a substrate.

FIG. 2 depicts one embodiment of a pin assembly 50 suitable for practice with the system depicted in FIG. 1 which includes the pressure controller 28. In the depicted embodiment, the pin assembly 50 includes a housing formed from an upper portion 52 and a lower portion 54 that are joined together by the screws 56A and 56B to define an interior chamber volume 58. FIG. 2 further depicts that to fluidicly seal the interior chamber volume 58 the housing can include a seal element depicted in FIG. 2 as an O-ring gasket 60 that sits between the upper block and the lower block 54 and surrounds completely the perimeter of the interior chamber volume 58. FIG. 2 further depicts that the pin assembly 50 includes a plurality of vesicles 62A–62D, each of which include an axial bore extending therethrough to form the depicted holding chambers 64A–64D. Each of the depicted vesicles extends through a respective aperture 68A–68D disposed within the lower block 54 of the housing.

As further shown in the depicted embodiment, each of the vesicles 62A–62D has an upper flange portion that sits against a seal element 70A–70D to form a fluid-tight seal between the vesicle and the lower block 54 to prevent fluid from passing through the apertures 68A–68D. To keep the seal tight, the depicted pin assembly 50 further includes a set of biasing elements 74A–74D depicted in FIG. 2 as springs which, in the depicted embodiments, are in a compressed state to force the flange element of the vesicles 62A–62D against their respective seal elements 70A–70D. As shown in FIG. 2, the biasing elements 74A–74D extend between the vesicles and the upper block 52. Each of the springs 74A–74D can be fixedly mounted to a mounting pad 76A–76D where the spring elements can attach to the upper block 52. The upper block 52 further includes an aperture 78 depicted in FIG. 2 as a centrally disposed aperture that includes a threaded bore for receiving a tube fitting (swagelok) 80 that can be rotatably mounted within the aperture 78.

As further depicted in FIG. 2, the swagelok 80 attaches by a conduit to a valve 82 than can connect the swagelok 80 to a conduit 84 that can be coupled to a pressure source, or alternatively can couple the swagelok 80 to a conduit 86 that provides for venting of the interior chamber 58. A central bore 88 extends through the swagelok 80 and couples to the tubing element which further connects to the valve 82 to thereby fluidicly and selectively couple the interior chamber volume 58 to either a pressure source, or a venting outlet.

The pin assembly 50 described above and depicted in FIG. 2 is disposed above a substrate element 90 that includes a plurality of wells 92 that are etched into the upper surface of the substrate 90. As illustrated by FIG. 2, the pitch of the vesicles 62A–62D is such that each vesicle is spaced from the adjacent vesicles by a distance that is an integral multiple of the pitch distance between wells 92 etched into the upper surface of the substrate 90. As will be seen from the following description, this spacing facilitates the parallel dispensing of fluid, such that fluid can be dispensed into a plurality of wells in a single operation. Each of the vesicles can be made from stainless steel, silica, polymeric material or any other material suitable for holding fluid sample. In one example, 16 vesicles are employed in the assembly, which are made of hardened beryllium copper, gold plated over nickel plate. They are 43.2 mm long and the shaft of the vesicle is graduated to 0.46 mm outer diameter with a concave tip. Such a pin was chosen since the pointing accuracy (distance between the center of adjacent tips) can be approximately 501 micrometers. However, it will be apparent that any suitable pin style can be employed for the device, including but not limited to flat, star-shaped, concave, pointed solid, pointed semi-hollow, angled on one or both sides, or other such geometries.

Figure 3:
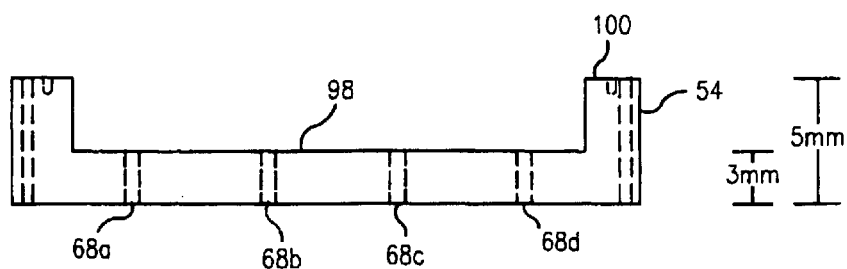
FIG. 3 depicts a bottom portion of the assembly shown in FIG. 2.

FIG. 3 shows from a side perspective the lower block 54 of the pin assembly 50 depicted in FIG. 2. FIG. 3 shows approximate dimensions for an exemplary suitable pin assembly. As shown, the lower block 54 has a bottom plate 98 and a surrounding shoulder 100. The bottom plate 98 is approximately 3 mm in thickness and the shoulder 100 is approximately 5 mm in thickness.

Figure 4:
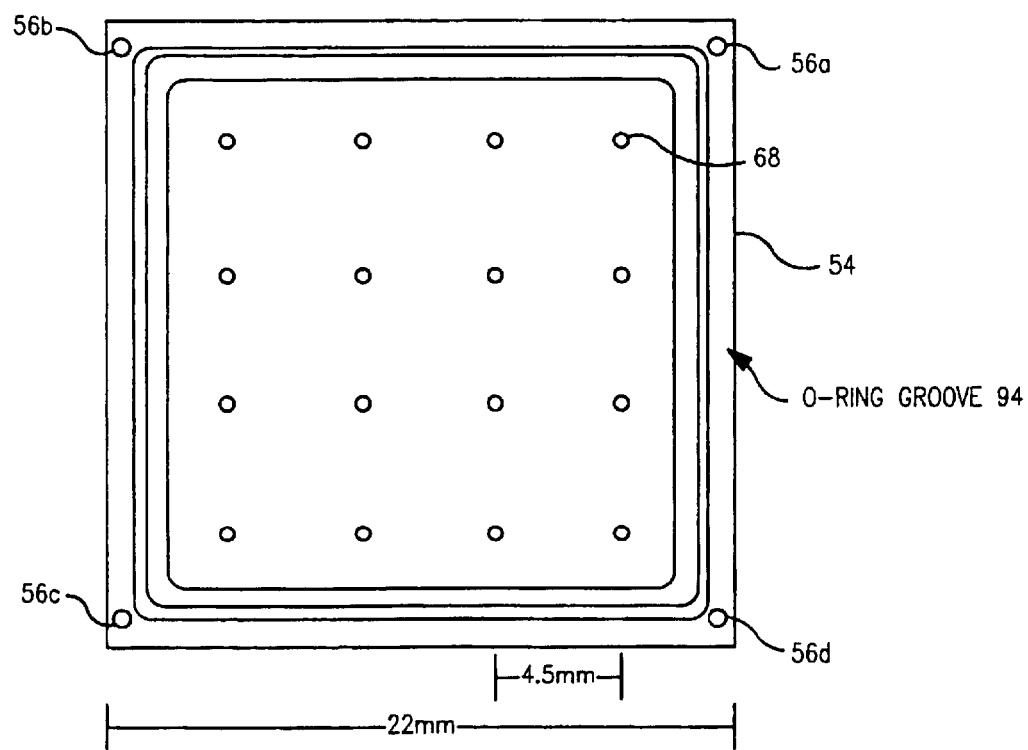
FIG. 4 depicts an alternative view of the bottom portion of the pin assembly depicted in FIG. 2.

FIG. 4 shows from an overhead perspective the general structure and dimensions for one lower block 54 suitable for use with the pin assembly 50 shown in FIG. 2. As shown in FIG. 4, the lower block 54 includes a four-by-four matrix of apertures 68 to provide 16 apertures each suitable for receiving a vesicle. As described above with reference to FIG. 2, the spacing between the aperture 68 is typically an integral multiple of the distance between wells on a substrate surface as well as the wells of a source plate. Accordingly, a pin assembly having the lower block 54 as depicted in FIG. 4 can dispense fluid in up to 16 wells simultaneously. FIG. 4 also shows general dimensions of one lower block 54 such that each side of block 54 is generally 22 mm in length and the pitch between aperture 68 is approximately 4.5 mm. Such a pitch is suitable for use with a substrate where fluid is to be dispensed at locations approximately 500 μm apart, as exemplified by the substrate 90 of FIG. 2. FIG. 4 also shows that the lower block 54 can include an optional O-ring groove 94 adapted for receiving an O-ring seal element, such as the seal element 60 depicted in FIG. 2. It is understood that such a groove element 94 can enhance and improve the fluid seal formed by the seal element 60.

The pinblock can be manufactured of stainless steel as this material can be drilled accurately to about +25 μm, but a variety of probe materials can also be used, such as G10 laminate, PMMA or other suitable material. The pin block can contain any number of apertures and is shown with 16 receptacles which hold the 16 pins in place. To increase the pointing accuracy of each pin, an optional alignment place can be placed below the block so that about 6 mm of the pin tip is left exposed to enable dipping into the wells of a microtiter plate. The layout of the probes in the depicted tool is designed to coordinate with a 384-well microtiter plate, thus the center-to-center spacing of the probes in 4.5 mm. An array of 4×4 probes was chosen since it would produce an array that would fit in less than one square inch, which is the travel range of an xy stage of a MALDI TOF MS employed by the assignee. The pintool assembly is completed with a stainless steel cover on the top side of the device which is then attached onto the Z-arm of the robot.

With references to FIG. 5, the operation of one embodiment of the systems, substrates and methods provided herein can be explained. In this exemplary embodiment, the robotic assembly 16 employs a pin tool assembly 38 that is configured similarly as the pin tool assembly 50 depicted in FIG. 2. The pressure controller 28 selectively controls the pressure within chamber 58. With this embodiment, a control program operates on the data processor 12 to control the robotic assembly 16 in a way that the assembly 16 prints an array of elements on the substrates 34.

Figure 5A:
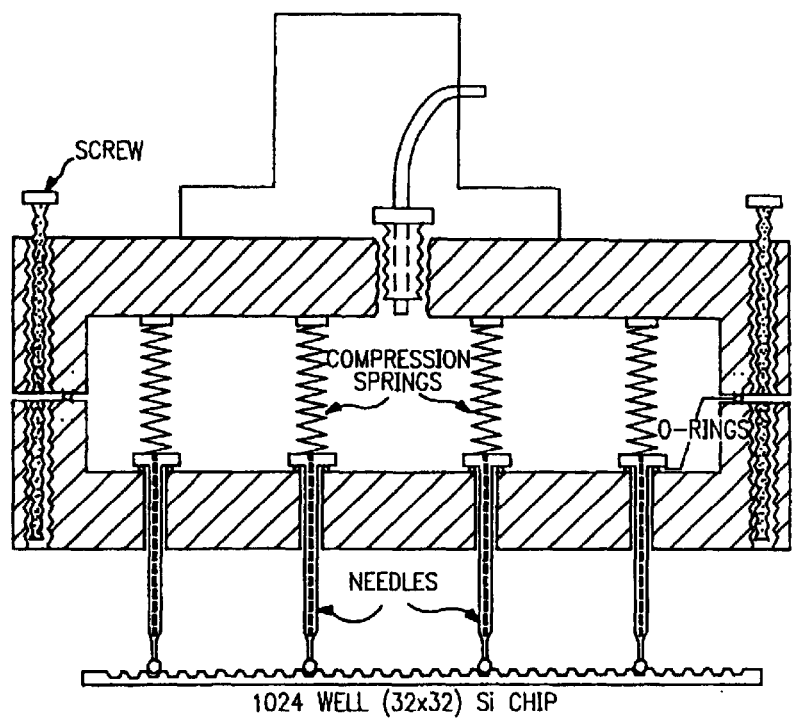
FIGS. 5A–5D depicts one method provided herein for preparing an array of sample material.

In a first step, FIG. 5A, the program can direct the robotic assembly 16 to move the pin assembly 38 to be disposed above the source plate 20. The robotic assembly 16 will then dip the pin assembly into the source plate 20 which can be a 384 well DNA source plate. As shown in FIG. 4 the pin assembly can include 16 different pins such that the pin assembly 50 will dip 16 pins into different 16 wells of the 384 well DNA source plate 20. Next the data processor 12 will direct the motion controller 14 to operate the robotic assembly 16 to move the pin assembly to a position above the surface of the substrate 34. The substrate 34 can be any substrate suitable for receiving a sample of material and can be formed of silicon, plastic, metal, or any other such suitable material. Optionally the substrate will have a flat surface, but can alternatively include a pitted surface, a surface etched with wells or any other suitable surface typography. The program operating on data processor 12 can then direct the robotic assembly, through the motion controller 14, to direct the pressure controller 28 to generate a positive pressure within the interior chamber volume 58. In this practice, the positive interior pressure will force fluid from the holding chambers of vesicles 62a-62d to eject fluid from the vesicles and into a respective well 92 of the substrate 90.

In this embodiment, the program operating on data processor 12 can also direct the controller 14 to control the pressure controller 28 to control filling the holding chambers with source material from the source plate 20. The pressure controller 28 can generate a negative pressure within the interior chamber volume 58 of the pin assembly. This will cause fluid to be drawn up into the holding chambers of the vesicles 62A–62D. The pressure controller 28 can regulate the pressure either by open-loop or closed-loop control to avoid having fluid overdrawn through the holding chambers and spilled into the interior chamber volume 58. Loop control systems for controlling pressure are well known in the art and any suitable controller can be employed. Such spillage could cause cross-contamination, particularly if the source material drawn from the source plate 20 varies from well to well.

In an alternative embodiment, each of the holding chambers 64A–64D is sufficiently small to allow the chambers to be filled by capillary action. In such a practice, the pin assembly can include an array of narrow bore needles, such as stainless steel needles, that extend through the apertures of the lower block 54. The needles that are dipped into source solutions will be filled by capillary action. In one practice, the length of capillary which is to be filled at atmospheric pressure is determined approximated by:

$$H = \frac{2y}{PGR}$$

where H equals Height, gamma equbTs surface tension, P equals solution density, G equals gravitational force and R equals needle radius. Thus the volume of fluid held by each vesicle can be controlled by selecting the dimensions of the interior bore. It is understood that at room temperature water will fill a 15 cm length of 100 µm radius capillary. Thus, a short bore nanoliter volume needle will fill to full capacity, but should not overflow because the capillary force is understood to be too small to form a meniscus at the top of the needle orifice. This prevents cross-contamination due to spillage. In one embodiment, the vesicles of the pin assembly can be provided with different sized interior chambers for holding and dispensing different volumes of fluid.

In an alternative practice, to decrease the volume of liquid that is drawn into the holding chambers of the vesicles, a small positive pressure can be provided within the interior chamber volume 58 by the pressure controller 28. The downward force created by the positive pressure can be used to counter the upward capillary force. In this way, the volume of fluid that is drawn by capillary force into the holding chambers of the vesicles can be controlled.

Figure 5B:
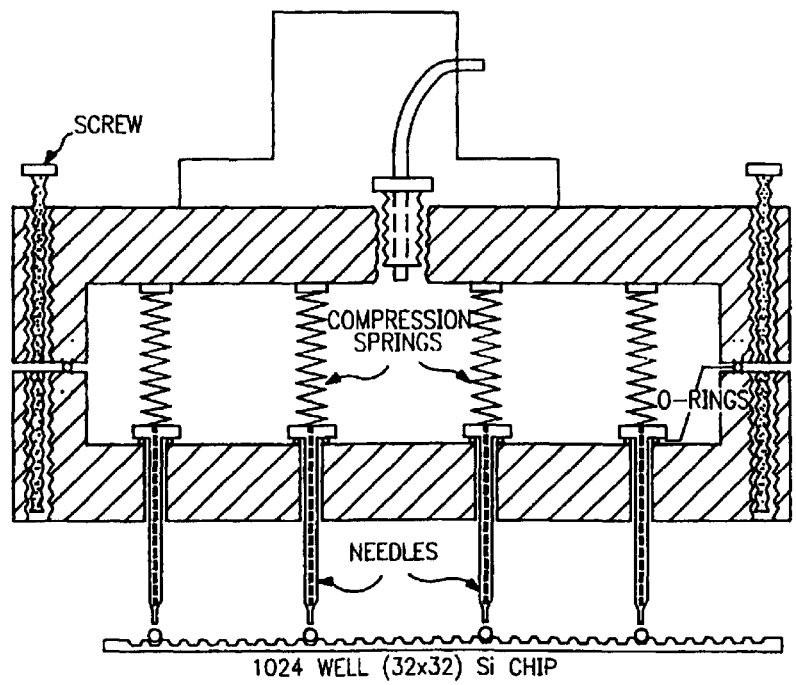

FIG. 5B, shows that fluid within the holding chambers of the needle can be dispensed by a small positive pressure introduced through the central bore 88 extending through a swagelok 80. By regulating the pressure pulse that is introduced into the interior chamber volume 58, fluid can be ejected either as a spray or by droplet formation at the needle tip. It is understood that the rate of dispensing, droplet versus spray, depends in part upon the pressure applied by the pressure controller 28. In one practice, pressure is applied in the range of between 10 and 1,000 Torr of atmospheric pressure.

To this end the data processor 12 can run a computer program that controls and regulates the volume of fluid dispensed. The program can direct the controller 28 to eject a defined volume of fluid, either by generating a spray or by forming a drop that sits at the end of the vesicle, and can be contacted with the substrate surface for dispensing the fluid thereto.

Figure 5C:
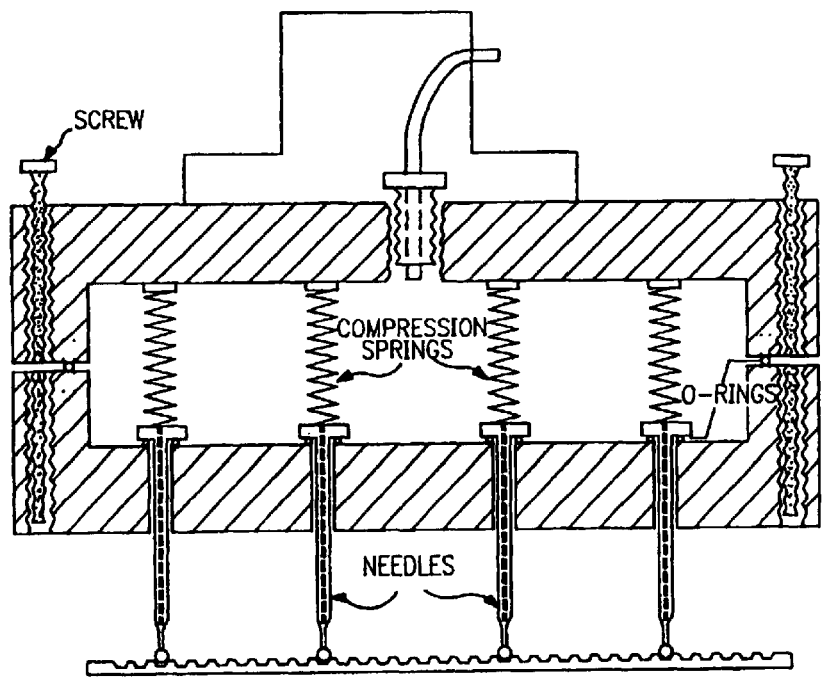
Figure 5D:
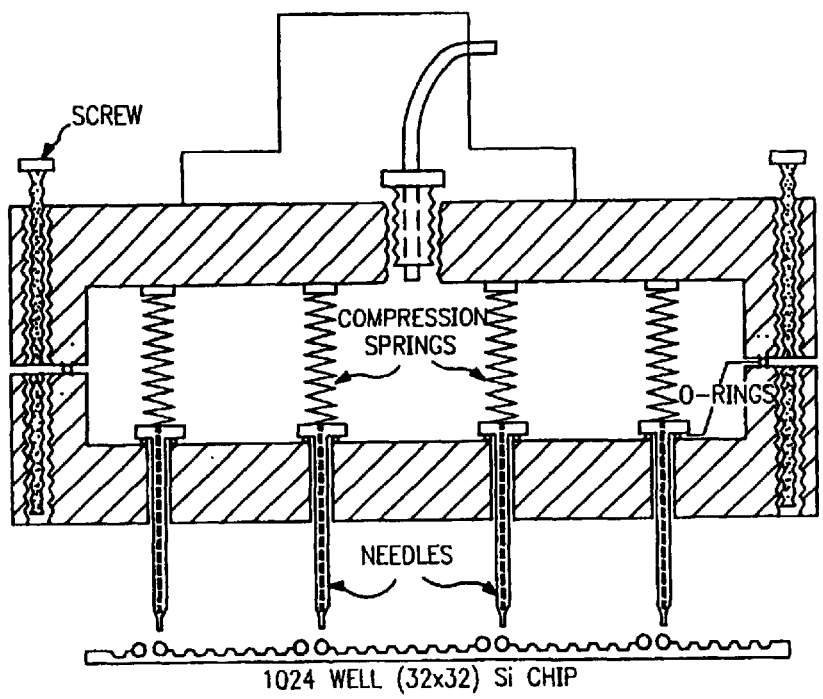

FIGS. 5C and 5D show the earlier steps shown in FIGS. 5A–5B can again be performed, this time at a position on the substrate surface that is offset from the earlier position. In the depicted process, the pin tool is offset by a distance equal to the distance between two wells 92. Other offset printing techniques can be employed.

It will be understood that several advantages of the pin assembly depicted in FIG. 2 are achieved. For example, rinsing between dispensing events is straightforward, requiring only single or multiple pin fillings and emptying events with a rinse solution. Moreover, since all holding chambers fill to full capacity, the accuracy of the volumes dispensed varies only according to needle inner dimensions which can be carefully controlled during pin production. Further the device is cost effective, with the greatest expense attributed to the needles, however because no contact with a surface is required, the needles are exposed to little physical strain or stress, making replacement rare and providing long life.

Alternatively, deposition of sample material onto substrate surface can include techniques that employ pin tool assemblies that have solid pin elements extending from a block wherein a robotic assembly dips the solid pin elements of the pin assembly into a source of sample material to wet the distal ends of the pins with the sample materials. Subsequently the robotic assembly can move the pin assembly to a location above the surface the substrate and then lower the pin assembly against the surface of the substrate to contact the individual wetted pins against the surface for spotting material of the substrate surface.

Figure 6A:
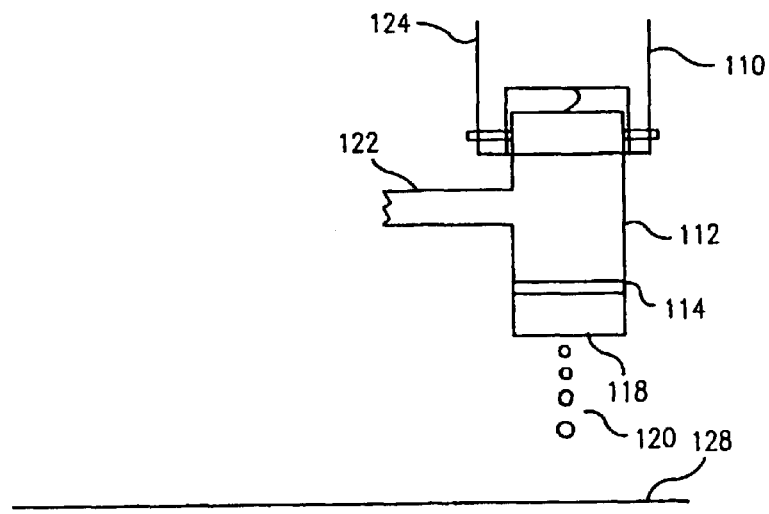
FIGS. 6A–6B depict an alternative assembly for dispensing material to the surface of a substrate.
Figure 6B:
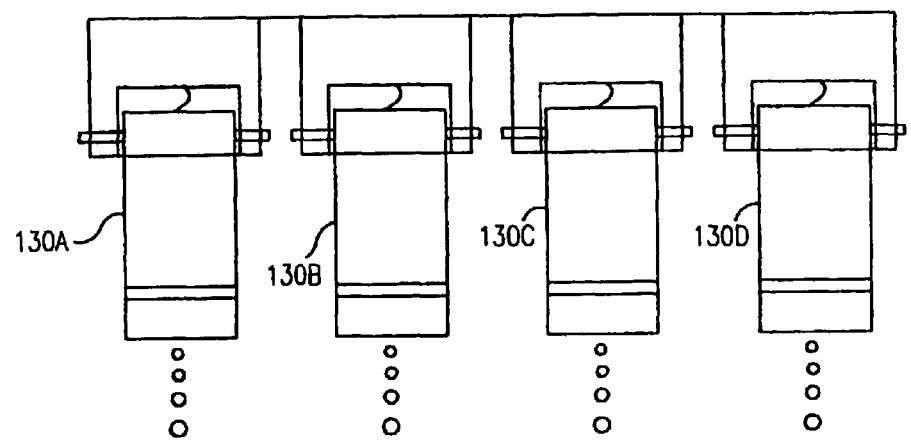

FIGS. 6A and 6B depict another alternative system for dispensing material on or to the surface of the substrate. In particular, FIG. 6A depicts a jet printing device 110 which includes a capillary element 112, a transducer element 114 and orifice (not shown) 118, a fluid conduit 122, and a mount 124 connecting to a robotic arm assembly, such as the robotic arm 24 depicted in FIG. 1. As further shown in FIG. 6A the jet assembly 110 is suitable for ejecting from the orifice 118 a series of drops 120 of a sample material for dispensing sample material onto the surface 128.

The capillary 112 of the jet assembly 110 can be a glass capillary, a plastic capillary, or any other suitable housing that can carry a fluid sample and that will allow the fluid sample to be ejected by the action of a transducer element, such as the transducer element 114. The transducer element 114 depicted in FIG. 6A is a piezo electric transducer element which forms around the parameter of the capillary 112 and can transform an electrical pulse received from the pulse generator within a robotic assembly 16 to cause fluid to eject from the orifice 118 of the capillary 112. One such jet assembly having a piezoelectric transducer element is manufactured by Microdrop GmbH of Germany. Any jet assembly that is suitable for dispensing defined and controlled the volumes of fluid can be used in the methods, including those that use piezoelectric transducers, electric transducers, electrorestrictive transducers, magnetorestrictive transducers, electromechanical transducers, or any other suitable transducer element. In the depicted embodiment, the capillary 112 has a fluid conduit 122 for receiving fluid material. In an optional embodiment, fluid can be drawn into the capillary by action of a vacuum pressure that will draw fluid through the orifice 118 when the orifice 118 is submerged in a source of fluid material. Other embodiments of the jet assembly 110 can be employed.

FIG. 6B illustrates a further alternative assembly suitable for use in the methods provided herein, and suitable for being carried on the robotic arm of a robotic assembly, such as the assembly 16 depicted in FIG. 1. FIG. 6B illustrates four jet assemblies connected together, 130A–130D. Similar to the pin assembly in FIG. 2, the jet assembly depicted in FIG. 6B can be employed for the parallel dispensing of fluid material. It will be apparent to one of skill in the art of electrical engineering, that each of the jet assemblies 130A–130D can be operated independently of the others, for allowing the selective dispensing of fluid from select ones of the jet assemblies. Moreover, each of the jet assemblies 130A–130D can be independently controlled to select the volume of fluid that is dispensed from each respected one of the assembly 130A–130D. Other modifications and alterations can be made to the assembly depicted in FIG. 6B without departing from the scope of the invention.

In another aspect, methods for rapidly analyzing sample materials are provided. To this end sample arrays can be formed on a substrate surface according to any of the techniques discussed above. The sample arrays are then analyzed by mass spectrometry to collect spectra data that is representative of the composition of the samples in the array. It is understood that the above methods provide processes that allow for rapidly dispensing definite and controlled volumes of analyte material. In particular these processes allow for dispensing sub to low nanoliter volumes of fluid. These low volume deposition techniques generate sample arrays well suited for analysis by mass spectrometry. For example, the low volumes yield reproducibility of spot characteristics, such as evaporation rates and reduced dependence on atmospheric conditions such as ambient temperature and light.

Continuing with the example showing in FIG. 1, the arrays can be prepared by loading oligonucleotides (0.1–50 μl) of different sequences or concentrations into the wells of a 96 well microtiter source plate 20; the first well can be reserved for holding a matrix solution. A substrate 34, such as a pitted silicon chip substrate, can be placed on the stage 26 of the robotics assembly 16 and can be aligned manually to orient the matrix of wells about a set of reference axes. The control program executing on the data processor 12 can receive the coordinates of the first well of the source plate 20. The robotic arm 24 can dip the pin assembly 38 into source plate 20 such that each of the 16 pins is dipped into one of the wells. Each vesicle can fill by capillary action so that the full volume of the holding chamber contains fluid. Optionally, the program executing on the data processor 12 can direct the pressure controller to fill the interior chamber 58 of the pin assembly 38 with a positive bias pressure that will counteract, in part, the force of the capillary action to limit or reduce the volume of fluid that is drawn into the holding chamber.

Optionally, the pin assembly 38 can be dipped into the same 16 wells of the source plate 20 and spotted on a second target substrate. This cycle can be repeated on as many target substrates as desired. Next the robotic arm 24 can dip the pin assembly 38 in a washing solution, and then dip the pin assembly into 16 different wells of the source plate 20, and spot onto the substrate target offset a distance from the initial set of 16 spots. Again this can be repeated for as many target substrates as desired. The entire cycle can be repeated to make a 2×2 array from each vesicle to produce an 8×8 array of spots (2×2 elements/vesicle×16 vesicles=64 total elements spotted). However, it will be apparent to anyone of skill in the art that other process suitable for forming arrays can be employed.

In an alternative embodiment, oligonucleotides of different sequences or concentrations can be loaded into the wells of up to three different 384-well microtiter source plates; one set of 16 wells can be reserved for matrix solution. The wells of two plates are filled with washing solution. Five microtiter plates can be loaded onto the stage of the robotic assembly 16. A plurality of target substrates can be placed abutting an optional set of banking or registration pins disposed on the stage 26 and provided for aligning the target substrates along a set of reference axes. If the matrix and oligonucleotide are not pre-mixed, the pin assembly can be employed to first spot matrix solution on all desired target substrates. In a subsequent step the oligonucleotide solution can be spotted in the same pattern as the matrix material to re-dissolve the matrix. Alternatively, a sample array can be made by placing the oligonucleotide solution on the wafer first, followed by the matrix solution, or by pre-mixing the matrix and oligonucleotide solutions.

After depositing the sample arrays onto the surface of the substrate, the arrays can be analyzed using any of a variety of means (e.g., spectrometric techniques, such as UV/VIS, IR, fluorescence, chemiluminescence, NMR spectrometry or mass spectrometry. For example, subsequent to either dispensing process, sample loaded substrates can be placed onto a MALDI-TOF source plate and held there with a set of beveled screw mounted polycarbonate supports. In one practice, the plate can be transferred on the end of a probe to be held onto a 1 μm resolution, 1" travel xy stage (Newport) in the source region of a time-of-flight mass spectrometer. It will be apparent to one of skill in the art that any suitable mass spectrometry tool can be employed.

Preferred mass spectrometer formats include ionization (I) techniques including but not limited to matrix assisted laser desorption (MALDI), continuous or pulsed electrospray (ESI) and related methods (e.g. Ionspray or Thermospray), or massive cluster impact (MCI); those ion sources can be matched with detection formats including linear or non-linear reflectron time-of-flight (TOF), single or multiple quadruple, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed. Subattomole levels of protein have been detected for example, using ESI (Valaskovic, G. A. et al., (1996) *Science* 273: 1199–1202) or MALDI (Li, L. et al., (1996) *J. Am. Chem. Soc* 118: 1662–1663) mass spectrometry.

Thus, it will be understood that in processes provided herein a completely non-contact, high-pressure spray or partial-contact, low pressure droplet formation mode can be employed. In the latter, the only contact that will occur is between the droplet and the walls of the well or a hydrophilic flat surface of the substrate 34. However, in neither practice need there be any contact between the needle tip and the surface.

Definitions

As used herein the following terms and phrases shall have the meanings set forth below:

As used herein, the term "nucleic acid" refers to oligonucleotides or polynucleotides such as deoxyribonucleic acid DNA) and ribonucleic acid (RNA) as well as analogs of either RNA or DNA, for example made from nucleotide analog, any of which are in single or double stranded form, Nucleic acid molecules can by synthetic or can be isolated from a particular biological sample using any of a number or procedures which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules for urine; and proteinase K extraction can be used to obtain nucleic acid from blood (Rolff, A. et al. PCR: Clinical Diagnostics and Research, Springer (1994)).

The terms "protein", "polypeptide" and "peptide" are used interchangeably herein when referring to a translated nucleic acid (e.g. a gene product).

"Sample" as used herein, shall refer to a composition containing a material to be detected. In a preferred embodiment, the sample is a "biological sample" (i.e., any material obtained from a living source (e.g. human, animal, plant, bacteria, fungi, protist, virus). The biological sample can be in any form, including solid materials (e.g. tissue, cell pellets and biopsies) and biological fluids (e.g. urine, blood, saliva, amniotic fluid and mouth wash (containing buccal cells)). Preferably solid materials are mixed with a fluid.

"Substrate" shall mean an insoluble support onto which a sample is deposited. Examples of appropriate substrates include beads (e.g., silica gel, controlled pore glass, magnetic, Sephadex/Sepharose, cellulose), capillaries, flat supports such as glass fiber filters, glass surfaces, metal surfaces (steel, gold, silver, aluminum, copper and silicon), plastic materials including multiwell plates or membranes (e.g., of polyethylene, polypropylene, polyamide, polyvinylidenedifluoride), pins (e.g., arrays of pins suitable for combinatorial synthesis or analysis or beads in pits of flat surfaces such as wafers (e.g., silicon wafers) with or without plates.

EXAMPLES

Robot-driven serial and parallel pL-nL dispensing tools were used to generate $10-10^3$ element DNA arrays on <1" square chips with flat or geometrically altered (e.g. with wells) surfaces for matrix assisted laser desorption ionization mass spectrometry analysis. In the former, a 'piezoelectric pipette' (70 μm id capillary) dispenses single or multiple-0.2 nL droplets of matrix, and then analyte, onto the chip; spectra from as low as 0.2 fmol of a 36-mer DNA have been acquired using this procedure. Despite the fast (<5 sec) evaporation, micro-crystals of 3-hydroxypicolinic acid matrix containing the analyte are routinely produced resulting in higher reproducibility than routinely obtained with larger volume preparations; all of 100 five fmol sports of a 23-mer in 800 μm wells yielded easily interpreted mass spectra, with 99/100 parent ion signals having signal to noise ration of >5. In a second approach, probes from 384 well microtiter plate are dispensed 16 at a time into chip wells or onto flat surfaces using an array of spring loaded pins which transfer-20 nL to the chip by surface contact; MS analysis of array elements deposited with the parallel method are comparable in terms of sensitivity and resolution to those made with the serial method.

I. Description of the piezoelectric serial dispenser. The experimental system built on a system purchased from Microdrop GmbH, Norderstedt Germany and includes a piezoelectric element driver which sends a pulsed signal to a piezoelectric element bonded to and surrounding a glass capillary which holds the solution to be dispensed; a pressure transducer to load (by negative pressure) or empty (by positive pressure) the capillary; a robotic xyz stage and robot driver to maneuver the capillary for loading, unloading, dispensing, and cleaning, a stroboscope and driver pulsed at the frequency of the piezo element to enable viewing of 'suspended' droplet characteristics; separate stages for source and designation plates or sample targets (i.e. Si chip); a camera mounted to the robotic arm to view loading to designation plate; and a data station which controls the pressure unit, xyz robot, and piezoelectric driver.

II. Description of the parallel dispenser. The robotic pintool includes 16 probes housed in a probe block and mounted on an X Y, Z robotic stage. The robotic stage was a gantry system which enables the placement of sample trays below the arms of the robot. The gantry unit itself is composed of X and Y arms which move 250 and 400 mm, respectively, guided by brushless linear servo motors with positional feedback provided by linear optical encoders. A lead screw driven Z axis (50 mm vertical travel) is mounted to the xy axis slide of the gantry unit and is controlled by an in-line rotary servo motor with positional feedback by a motor-mounted rotary optical encoder. The work area of the system is equipped with a slide-out tooling plate that holds five microtiter plates (most often, 2 plates of wash solution and 3 plates of sample for a maximum of 1152 different oligonucleotide solutions) and up to ten 20×20 mm wafers. The wafers are placed precisely in the plate against two banking pins and held secure by vacuum. The entire system is enclosed in plexi-glass housing for safety and mounted onto a steel support frame for thermal and vibrational damping. Motion control is accomplished by employing a commercial motion controller which was a 3-axis servo controller and is integrated to a computer; programming code for specific applications is written as needed.

Samples were dispensed with the serial system onto several surfaces which served as targets in the MALDI TOF analysis including [1] A flat stainless steel sample target as supplied for routine use in a Thermo Bioanalysis Vision 2000; [2] the same design stainless steel target with micromachined nanopits; [3] flat silicon (Si) wafers; [4] polished flat Si wafers; [5] Si wafers with rough (3–6 pLm features) pits; [6](a) 12×12 or ((b) 18×18) mm Si chips with (a) 10×10 (or (b) 16×16) arrays of chemically etched wells, each 800×8001 lm on a side with depths ranging from 99–400 (or(b) 120) micrometer, pitch (a) 1.0 (or(b) 1.125 mm); [7] 15×15 mm Si chips with 28×28 arrays of chemically etched wells, each 450×450 micrometer on a side with depths ranging from 48–300 micrometer, pitch 0.5 mm; [8]flat polycarbonate or other plastics; [9] gold and other metals; [10] membranes; [11] plastic surfaces sputtered with gold or other conducting materials. The dispensed volume is controlled from $10^{-10}$ to $10^{-6}$ L by adjusting the number of droplets dispensed.

Sample Preparation and Dispensing: Serial Oligonucleotides (0.1–50 ng/microliter of different sequence or concentrations were loaded into wells of a 96 well microtiter plate; the first well was reserved for matrix solution. A pitted chip (target 6a in MALDI targets' section) was placed on the stage and aligned manually. Into the (Windows-based) robot control software were entered the coordinates of the first well, the array size (ie number of spots in x and y) and spacing between elements, and the number of 0.2 nL drops per array element. The capillary was filled with ~10 microliters of rinse $H_2O$, automatically moved in view of a strobe light-illuminated camera for checking tip integrity and cleanliness while in continuous pulse mode, and emptied. The capillary was then filled with matrix solution, again checked at the stroboscope, and then used to spot an array onto flat or pitted surfaces. For reproducibilty studies in different MS modes, typically a 10×10 array of 0.2–20 nL droplets were dispensed. The capillary was emptied by application of positive pressure, optionally rinsed with $H_2O$, and let to the source oligo plate where ~5 μL of 0.05–2.0 μM synthetic oligo were drawn. The capillary was then rastered in a series over each of the matrix spots with 0.2–20 nL aqueous solution added to each.

Sample Preparation and Dispensing: Parallel Programs were written to control array making by offset printing; to make an array of 64 elements on 10 wafers, for example, the tool was dipped into 16 wells of a 384 well DNA source plate, moved to the target (e.g. Si, plastic, metal), and the sample spotted by surface contact. The tool was then dipped into the same 16 wells and spotted on the second target; this cycle was repeated on all ten wafers. Next the tool was dipped in washing solution, then dipped into 16 different wells of the source plate, and spotted onto the target 2.25 mm offset from the initial set of 16 spots; again this as repeated on all 10 wafers; the entire cycle was repeated to make a 2×2 array from each pin to produce an 8×8 array of spots (2×2 elements/pin×16 pins=64 total elements spotted).

To make arrays for MS analysis, oligonucleotides of different sequences or concentrations were loaded into the wells of up to three different 384-well microtiter plates, one set of 16 wells was reserved for matrix solution. The wells of two plates were filled with washing solution. The five microtiter plates were loaded onto the slide-out tooling plate. Ten wafers were placed abutting the banking pins on the tooling plate, and the vacuum turned on. In cases where matrix and oligonucleotide were not pre-mixed, the pintool was used to spot matrix solution first on all desired array elements of the ten wafers. For this example, a 16×16 array was created, thus the tool must spot each of the ten wafers 16 times, with an offset of 1.125 mm. Next, the oligonucleotide solution was spotted in the same pattern to re-dissolve the matrix, Similarly, an array could be made by placing the oligonucleotide solution on the wafer first, followed by the matrix solution, or by pre-mixing the matrix and oligonucleotide solutions.

Mass spectrometry. Subsequent to either dispensing scheme, loaded chips were held onto a MALDI-TOF source plate with a set of beveled screw mounted polycarbonated supports. The plate was transferred on the end of a probe to be held onto a 1 μm resolution, 1" travel xy stage (Newport) in the source region of a time-of-flight mass spectrometer. The instrument, normally operated with 18–26 kV extraction, could be operated in linear or curved field reflectron mode, and in continuous or delayed extraction mode.

Observations

I. Serial dispensing with the piezoelectric pipette. While delivery of a saturated 3 HPA solution can result in tip clogging as the solvent at the capillary-air interface evaporates, pre-mixing DNA and matrix sufficiently dilutes the matrix such that it remains in solution while stable sprays which could be maintained until the capillary was emptied were obtained; with 1:1 diluted (in $H_2O$) matrix solution, continuous spraying for >>10 minutes was possible. Turning off the piezo element so that the capillary sat inactive for >5 minutes, and reactivating the piezo element also did not result in a clogged capillary.

Initial experiments using stainless steel sample targets as provided by Finnigan Vision 2000 MALDI-TOF system run in reflectron mode utilized a pre-mixed solution of the matrix and DNA prior to dispensing onto the sample target. In a single microtiter well, 50 μL saturated matrix solution, 25 μL of a 51 μL solution of the 12-mer (ATCG)3, and 25 μL of a 51 μL solution of the 28-mer (ATCG)7 were mixed. A set of 10×10 arrays of 0.6 μL drops was dispensed directly onto a Finnigan Vision 2000 sample target disk; MALDI-TOF mass spectrum was obtained from a single array element which contained 750 attomoles of each of the two oligonucleotides. Interpretable mass spectra has been obtained for DNAs as large as a 53-mer (350 amol loaded, not shown) using this method.

Figure 7:
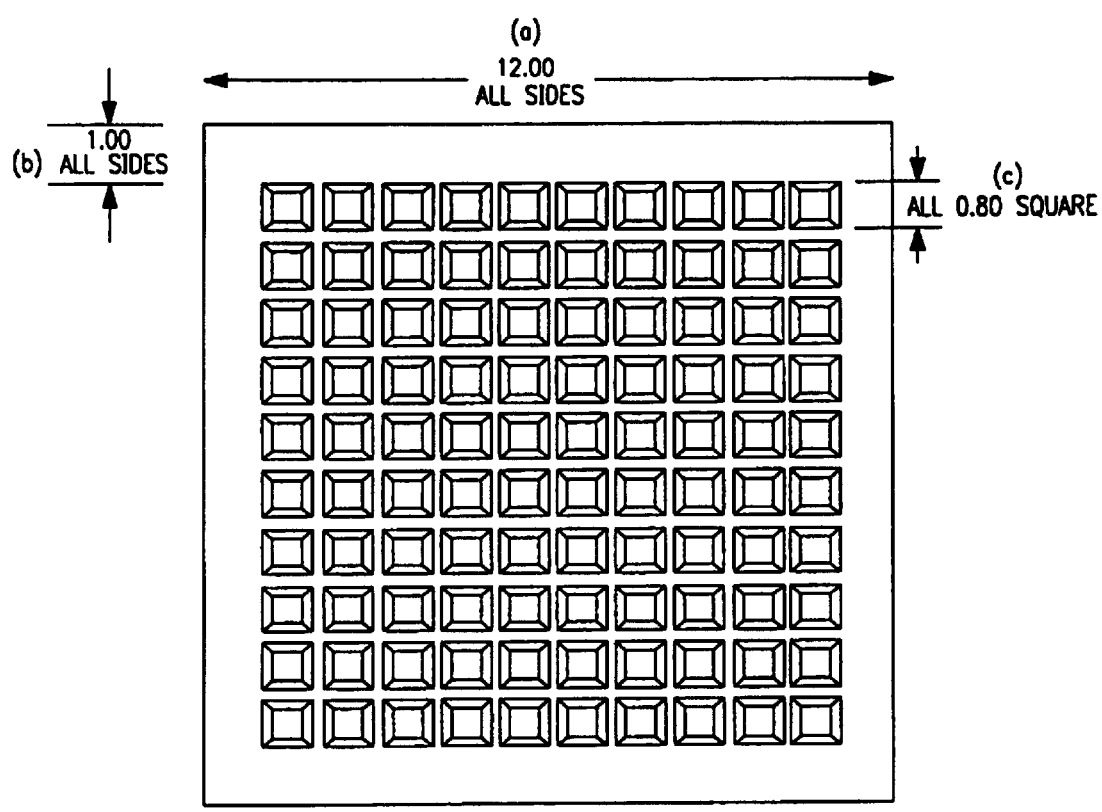
FIG. 7 depicts one embodiment of a substrate having wells etched therein that are suitable for receiving material for analysis.

Mass spectra were also obtained from DNAs microdispensed into the wells of a silicon chip. FIG. 7 shows a 12×12 mm silicon chip with 100 chemically etched wells; mask dimensions and etch time were set such that fustum (i.e., inverted flat top pyramidal) geometry wells with 800×800 μm (top surface) and 100 μm depth were obtained. Optionally, the wells can be roughed or pitted. As described above, the chip edge was aligned against a raised surface on the stage to define the x and y coordinate systems with respect to the capillary. (Alternatives include optical alignment, artificial intelligence pattern recognition routines, and dowel-pin based manual alignment). Into each well was dispensed 20 droplets (~5 nL) of 3-HPA matrix solution without analyte; for the 50% $CH_3CN$ solution employed, evaporation times for each droplet were on the order of 5–10 seconds. Upon solvent evaporation, each microdispensed matrix droplet as viewed under a 120× stereomicroscope generally appeared as an amorphous and 'milky' flat disk; such appearances are consistent with those of droplets from which the FIG. 3b spectrum was obtained. Upon tip emptying, rinsing, and refilling with a 1.4 μm aqueous solution of a 23-mer DNA (M,(calc)=6967 Da), the capillary was directed above each of the 100 spots of matrix where 5 nL of the aqueous DNA solution was dispensed directly on top of the matrix droplets. Employing visualization via a CCD camera, it appeared that the aqueous analyte solution mixed with and re-dissolved the matrix (complete evaporation took ~10 sec at ambient temperature and humidity). The amorphous matrix surfaces were converted to true micro-crystalline surfaces, with crystalline features on the order of <1 μm.

Figure 8:
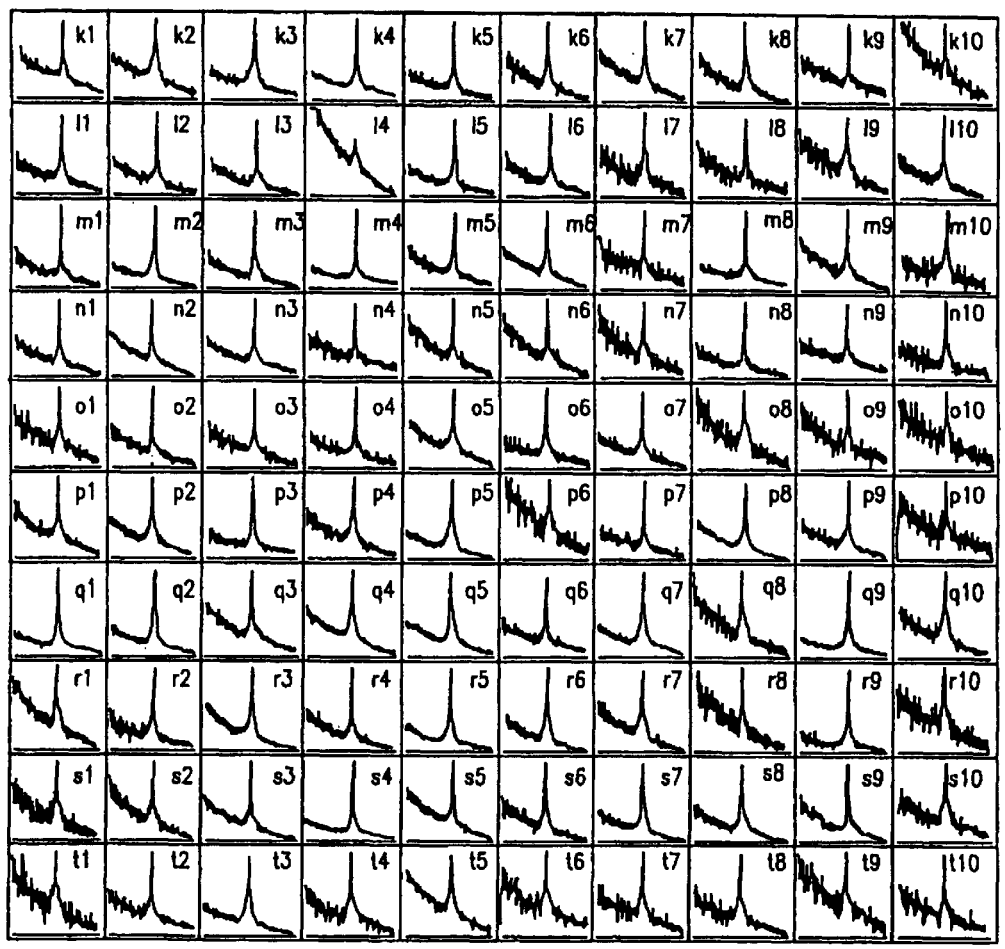
FIG. 8 depicts one example of spectra obtained from a linear time of flight mass spectrometer instrument and representative of the material composition of the sample material on the surface of the substrate depicted in FIG. 7.

Consistent with the improved crystallization afforded by the matrix re-dissolving method, mass spectrum acquisition appeared more reproducible than with pre-mixed matrix plus analyte solutions; each of the 100 five fmol spots of the 23-mer yielded interpreted mass spectra (FIG. 8), with 99/100 parent ion signals having signal to noise rations of >5; such reproducibility was also obtained with the flat silicon and metallic surfaces tried (not shown). The FIG. 8 spectra were obtained on a linear TOF instrument operated at 26 kV. Upon internal calibration of the top left spectrum (well 'k1') using the singly and doubly charged molecular ions, and application of this calibration file to all other 99 spectra as an external calibration (FIG. 9), a standard deviation of <9 Da from the average molecular weight was obtained, corresponding to a relative standard deviation of ~0.1%.

II. Parallel Dispensing with robotic pintool. Arrays were made with offset printing as described above. The velocity of the X and Y stages are 35 inches/sec, and the velocity of the Z stage is 5.5 inches/sec. It is possible to move the X and Y stages at maximum velocity to decrease the cycle times, however the speed of the Z stage is to be decreased prior to surface contact with the wafer to avoid damaging it. At such axes speeds, the approximate cycle time to spot 16 elements (one tool impression of the same solutions) on all ten wafers is 20 seconds, so to make an array of 256 elements would take 5.3 minutes. When placing different oligonucleotide solutions on the array, an additional washing step much be incorporated to clean the pin tip prior to dipping in another solution, thus the cycle time would increase to 25 seconds or 6.7 minutes to make 10 wafers.

Sample delivery by the tool was examined using radio-labeled solutions and the phosphorimager as described previously; it was determined that each pin delivers approximately 1 nL of liquid. The spot-to-spot reproducibility is high. An array of 256 oligonucleotide elements of varying sequence and concentration was made on flat silicon wafers using the pintool, and the wafer was analyzed by MALDI-TOF MS.

It will be understood that the above-described examples and illustrated embodiments are provided for describing the invention set forth herein and are not to be taken as limiting in any way, and the scope of the invention is to understood by the claims.

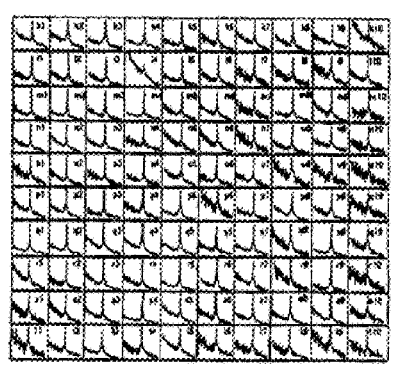

We claim:

1. A substrate, comprising a surface comprising material deposited at a plurality of discrete locations thereon thereby forming an array of spots thereon, wherein:
   the material comprises matrix material and a sample for matrix-assisted laser-desorption ionization (MALDI) mass spectrometric analysis;
   the material in each spot is in amount that results from deposition of a defined and controlled sub-nanoliter to low-nanoliter volume of a solution containing the material;
   MALDI mass spectra of the sample obtained directly from each spot are reproducible from spot to spot within the array of spots.

2. A substrate of claim 1, wherein the surface is flat.

3. A substrate of claim 1 having wells disposed on the surface, wherein the material is deposited in the wells.

4. A substrate of claim 3, wherein the wells have a rough interior surface.

5. A substrate of claim 1, wherein the surface is pitted.

6. A substrate of claim 5, that comprises pits with beads therein.

7. A substrate of claim 1, comprising an array of pins wherein the material is deposited on the end of the pin.

8. A substrate of claim 1, wherein the substrate comprises silica gel, controlled pore glass, magnetic beads, cross-linked dextrans, agarose, cellulose, glass, metal, or plastic.

9. A substrate of claim 8, wherein the metal is selected from the group consisting of steel, gold, silver aluminum and copper.

10. A substrate of claim 1, wherein the material further comprises a nucleic acid.

11. A substrate of claim 1, selected from the group consisting of capillaries, a capillary, a flat supports and membranes.

12. A substrate of claim 11, wherein the membrane comprises polyethylene, polypropylene, polyamide or polyvinylidenedifluoride.

13. A substrate of claim 1 that comprises silicon.

14. A substrate of claim 13 that is a silicon wafer.

15. The substrate of claim 13 that is a pitted silicon chip.

16. The substrate of claim 13 that comprises a hydrophilic flat surface.

17. A substrate of claim 1, wherein the surface of the substrate comprises metal, plastic, a membrane, polymeric material and a metal-grafted polymer.

18. A substrate of claim 1, wherein the surface of the substrate is functionalized chemically, functionalized with beads or functionalized with dendrite trees of captured material.

19. The substrate of claim 1, wherein the discrete locations are approximately 500 μm apart.

20. The substrate of claim 1 that comprises a hydrophilic flat surface.

21. A substrate of claim 1, wherein the material at each location is in an amount that results from deposition of a defined and controlled 0.2 to 20 nanoliter volume containing the material on the surface.

22. A substrate of claim 21, wherein the material further comprises a nucleic acid.

23. The substrate of claim 21 that comprises a hydrophilic flat surface.

24. The substrate of claim 23 that comprises silica gel, controlled pore glass, magnetic beads, cross-linked dextrans, agarose, cellulose, glass, metal, or plastic.

25. The substrate of claim 21 that comprises silicon.

26. The substrate of claim 25 that is a silicon wafer.

27. The substrate of claim 1, wherein the discrete locations are hydrophilic.

28. The substrate of claim 27 that comprises silica gel, controlled pore glass, magnetic beads, cross-linked dextrans, agarose, cellulose, glass, metal, or plastic.

29. The substrate of claim 27 that comprises silicon.

30. The substrate of claim 29 that is a silicon wafer.

31. The substrate of claim 27, wherein the material further comprises a nucleic acid.

* * * * *

UNITED STATES PATENT AND TRADEMARK OFFICE
CERTIFICATE OF CORRECTION

PATENT NO. : 7,232,688 B2
APPLICATION NO. : 09/364774
DATED : June 19, 2007
INVENTOR(S) : Daniel P. Little et al.

It is certified that error appears in the above-identified patent and that said Letters Patent is hereby corrected as shown below:

Please replace Claims 1 through 31 with the following Claims:

146 (New). A process for analyzing a nucleic acid analyte by matrix-assisted laser-desorption ionization (MALDI) mass spectrometry, which comprises:

(a) depositing a defined and controlled 0.2 to 20 nanoliter volume of a solution comprising a nucleic acid analyte onto a spot of a substrate having an array of the spots, wherein each spot of the substrate prior to step (a) comprises 3-hydroxypicolinic acid matrix and no analyte, and results from deposition of a defined and controlled 0.2 to 20 nanoliter volume of a solution comprising the matrix and a solvent and evaporation of the solvent;

(b) detecting the nucleic acid analyte deposited in step (a) by MALDI mass spectrometry.

147 (New). The process of claim 146, wherein the substrate comprises material selected from the group consisting of silica, glass, cellulose, silicon, metal, plastic, polymer and metal-grafted polymer.

148 (New). The process of claim 146, wherein the substrate comprises a flat surface, a flat surface with pits, a solid or porous bead, a membrane or a pin.

149 (New). The process of claim 146, wherein the substrate comprises silicon.

150 (New). The process of claim 146, wherein the substrate comprises a metal.

UNITED STATES PATENT AND TRADEMARK OFFICE
CERTIFICATE OF CORRECTION

| | |
|---|---|
| PATENT NO. | : 7,232,688 B2 |
| APPLICATION NO. | : 09/364774 |
| DATED | : June 19, 2007 |
| INVENTOR(S) | : Daniel P. Little et al. |

It is certified that error appears in the above-identified patent and that said Letters Patent is hereby corrected as shown below:

151 (New). The process of claim 146, wherein the substrate comprises a plastic.

152 (New). The process of claim 146, wherein the substrate comprises a membrane.

153 (New). The process of claim 146, wherein the substrate comprises a metal-grafted polymer.

154 (New). The process of claim 146, wherein the substrate is chemically functionalized.

155 (New). The process of claim 146, wherein the substrate is chemically functionalized with beads.

156 (New). The process of claim 146, wherein the substrate is chemically functionalized with a dendritic material.

157 (New). The process of claim 146, wherein each spot is a flat disk.

158 (New). The process of claim 146, wherein spectra of the MADLI mass spectrometry are reproducible with a relative standard deviation of about 0.1%.

159 (New). The process of claim 146, wherein the solvent comprises water.

160 (New). The process of claim 159, wherein the solvent is water.

161 (New). The process of claim 146, wherein the solvent comprises $CH_3CN$.

UNITED STATES PATENT AND TRADEMARK OFFICE
CERTIFICATE OF CORRECTION

| | | |
|---|---|---|
| PATENT NO. | : 7,232,688 B2 | |
| APPLICATION NO. | : 09/364774 | |
| DATED | : June 19, 2007 | |
| INVENTOR(S) | : Daniel P. Little et al. | |

It is certified that error appears in the above-identified patent and that said Letters Patent is hereby corrected as shown below:

162 (New). The process of claim 161, wherein the solvent is 50% $CH_3CN$.

163 (New). The process of claim 146, wherein the solution comprising the matrix consists essentially of the matrix.

164 (New). The process of claim 163, wherein the solution consists of the matrix.

165 (New). The process of claim 146, wherein the solution comprising the matrix is a saturated matrix solution.

166 (New). The process of claim 146, wherein the solution comprising the matrix is a diluted matrix solution.

167 (New). The process of claim 166, wherein the solution is a 1:1 diluted matrix solution.

168 (New). The process of claim 146, wherein the nucleic acid analyte is a deoxyribonucleic acid.

169 (New). The process of claim 146, wherein the nucleic acid analyte is a ribonucleic acid.

170 (New). The process of claim 146, wherein the nucleic acid analyte is single-stranded.

171 (New). The process of claim 146, wherein the nucleic acid analyte is double stranded.

UNITED STATES PATENT AND TRADEMARK OFFICE
CERTIFICATE OF CORRECTION

PATENT NO.        : 7,232,688 B2
APPLICATION NO. : 09/364774
DATED              : June 19, 2007
INVENTOR(S)       : Daniel P. Little et al.

It is certified that error appears in the above-identified patent and that said Letters Patent is hereby corrected as shown below:

172 (New). The process of claim 146, wherein the nucleic acid analyte is a nucleic acid analog.

173 (New). The process of claim 146, wherein the nucleic acid analyte contains a mutation.

174 (New). The process of claim 146, wherein the MALDI mass spectrometry comprises time of flight spectrometry.

175 (New). The process of claim 172, wherein the MALDI mass spectrometry comprises linear reflecton time of flight spectrometry.

176 (New). The process of claim 174, wherein the MALDI mass spectrometry comprises non-linear reflecton time of flight spectrometry.

177 (New). The process of claim 146, wherein the MALDI mass spectrometry comprises Fourier transform spectrometry.

178 (New). The process of claim 146, wherein the MALDI mass spectrometry comprises Fourier transform ion cyclotron resonance spectrometry.

179 (New). The process of claim 146, wherein the MALDI mass spectrometry comprises quadrupole spectrometry.

180 (New). The process of claim 179, wherein the MALDI mass spectrometry comprises single quadrupole spectrometry.

UNITED STATES PATENT AND TRADEMARK OFFICE
CERTIFICATE OF CORRECTION

| | |
|---|---|
| PATENT NO. | : 7,232,688 B2 |
| APPLICATION NO. | : 09/364774 |
| DATED | : June 19, 2007 |
| INVENTOR(S) | : Daniel P. Little et al. |

It is certified that error appears in the above-identified patent and that said Letters Patent is hereby corrected as shown below:

181 (New). The process of claim 179, wherein the MALDI mass spectrometry comprises multiple quadrupole spectrometry.

182 (New). The process of claim 146, wherein the MALDI mass spectrometry comprises magnetic sector spectrometry.

183 (New). The process of claim 182, wherein the MALDI mass spectrometry comprises single magnetic sector spectrometry.

184 (New). The process of claim 182, wherein the MALDI mass spectrometry comprises multiple magnetic sector spectrometry.

185 (New). The process of claim 146, wherein the MALDI mass spectrometry comprises ion trap spectrometry.

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

PATENT NO.        : 7,232,688 B2
APPLICATION NO.   : 09/364774
DATED             : June 19, 2007
INVENTOR(S)       : Daniel P. Little et al.

It is certified that error appears in the above-identified patent and that said Letters Patent is hereby corrected as shown below:

Delete the Title page and substitute therefor the attached title page.

Column 17, line 48 through Column 18, line 60,

Please replace Claims 1 through 31 with the following Claims:

1. A process for analyzing a nucleic acid analyte by matrix-assisted laser-desorption ionization (MALDI) mass spectrometry, which comprises:

(a) depositing a defined and controlled 0.2 to 20 nanoliter volume of a solution comprising a nucleic acid analyte onto a spot of a substrate having an array of the spots, wherein each spot of the substrate prior to step (a) comprises 3-hydroxypicolinic acid matrix and no analyte, and results from deposition of a defined and controlled 0.2 to 20 nanoliter volume of a solution comprising the matrix and a solvent and evaporation of the solvent;

(b) detecting the nucleic acid analyte deposited in step (a) by MALDI mass spectrometry.

2. The process of claim 1, wherein the substrate comprises material selected from the group consisting of silica, glass, cellulose, silicon, metal, plastic, polymer and metal-grafted polymer.

3. The process of claim 1, wherein the substrate comprises a flat surface, a flat surface with pits, a solid or porous bead, a membrane or a pin.

UNITED STATES PATENT AND TRADEMARK OFFICE
CERTIFICATE OF CORRECTION

PATENT NO. : 7,232,688 B2
APPLICATION NO. : 09/364774
DATED : June 19, 2007
INVENTOR(S) : Daniel P. Little et al.

It is certified that error appears in the above-identified patent and that said Letters Patent is hereby corrected as shown below:

4. The process of claim 1, wherein the substrate comprises silicon.

5. The process of claim 1, wherein the substrate comprises a metal.

6. The process of claim 1, wherein the substrate comprises a plastic.

7. The process of claim 1, wherein the substrate comprises a membrane.

8. The process of claim 1, wherein the substrate comprises a metal-grafted polymer.

9. The process of claim 1, wherein the substrate is chemically functionalized.

10. The process of claim 1, wherein the substrate is chemically functionalized with beads.

11. The process of claim 1, wherein the substrate is chemically functionalized with a dendritic material.

12. The process of claim 1, wherein each spot is a flat disk.

13. The process of claim 1, wherein spectra of the MALDI mass spectrometry are reproducible with a relative standard deviation of about 0.1%.

14. The process of claim 1, wherein the solvent comprises water.

15. The process of claim 14, wherein the solvent is water.

16. The process of claim 1, wherein the solvent comprises $CH_3CN$.

UNITED STATES PATENT AND TRADEMARK OFFICE
CERTIFICATE OF CORRECTION

PATENT NO. : 7,232,688 B2
APPLICATION NO. : 09/364774
DATED : June 19, 2007
INVENTOR(S) : Daniel P. Little et al.

It is certified that error appears in the above-identified patent and that said Letters Patent is hereby corrected as shown below:

17. The process of claim 16, wherein the solvent is 50% $CH_3CN$.

18. The process of claim 1, wherein the solution comprising the matrix consists essentially of the matrix.

19. The process of claim 18, wherein the solution consists of the matrix.

20. The process of claim 1, wherein the solution comprising the matrix is a saturated matrix solution.

21. The process of claim 1, wherein the solution comprising the matrix is a diluted matrix solution.

22. The process of claim 21, wherein the solution is a 1:1 diluted matrix solution.

23. The process of claim 1, wherein the nucleic acid analyte is a deoxyribonucleic acid.

24. The process of claim 1, wherein the nucleic acid analyte is a ribonucleic acid.

25. The process of claim 1, wherein the nucleic acid analyte is single-stranded.

26. The process of claim 1, wherein the nucleic acid analyte is double stranded.

UNITED STATES PATENT AND TRADEMARK OFFICE
CERTIFICATE OF CORRECTION

| | | |
|---|---|---|
| PATENT NO. | : 7,232,688 B2 | Page 4 of 6 |
| APPLICATION NO. | : 09/364774 | |
| DATED | : June 19, 2007 | |
| INVENTOR(S) | : Daniel P. Little et al. | |

It is certified that error appears in the above-identified patent and that said Letters Patent is hereby corrected as shown below:

27. The process of claim 1, wherein the nucleic acid analyte is a nucleic acid analog.

28. The process of claim 1, wherein the nucleic acid analyte contains a mutation.

29. The process of claim 1, wherein the MALDI mass spectrometry comprises time of flight spectrometry.

30. The process of claim 27, wherein the MALDI mass spectrometry comprises linear reflecton time of flight spectrometry.

31. The process of claim 29, wherein the MALDI mass spectrometry comprises non-linear reflecton time of flight spectrometry.

32. The process of claim 1, wherein the MALDI mass spectrometry comprises Fourier transform spectrometry.

33. The process of claim 1, wherein the MALDI mass spectrometry comprises Fourier transform ion cyclotron resonance spectrometry.

34. The process of claim 1, wherein the MALDI mass spectrometry comprises quadrupole spectrometry.

35. The process of claim 34, wherein the MALDI mass spectrometry comprises single quadrupole spectrometry.

UNITED STATES PATENT AND TRADEMARK OFFICE
CERTIFICATE OF CORRECTION

PATENT NO. : 7,232,688 B2
APPLICATION NO. : 09/364774
DATED : June 19, 2007
INVENTOR(S) : Daniel P. Little et al.

It is certified that error appears in the above-identified patent and that said Letters Patent is hereby corrected as shown below:

36. The process of claim 34, wherein the MALDI mass spectrometry comprises multiple quadrupole spectrometry.

37. The process of claim 1, wherein the MALDI mass spectrometry comprises magnetic sector spectrometry.

38. The process of claim 37, wherein the MALDI mass spectrometry comprises single magnetic sector spectrometry.

39. The process of claim 37, wherein the MALDI mass spectrometry comprises multiple magnetic sector spectrometry.

40. The process of claim 1, wherein the MALDI mass spectrometry comprises ion trap spectrometry.

This certificate supersedes the Certificate of Correction issued June 17, 2008.

Signed and Sealed this

Twenty-ninth Day of July, 2008

JON W. DUDAS
*Director of the United States Patent and Trademark Office*

(12) United States Patent
Little et al.

(10) Patent No.: US 7,232,688 B2
(45) Date of Patent: Jun. 19, 2007

(54) SYSTEMS AND METHODS FOR PREPARING AND ANALYZING LOW VOLUME ANALYTE ARRAY ELEMENTS

(75) Inventors: Daniel P. Little, Boston, MA (US); Maryanne J. O'Donnell-Maloney, Boston, MA (US); Charles R. Cantor, Boston, MA (US); Hubert Köster, La Jolla, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 09/364,774

(22) Filed: Jul. 30, 1999

(65) Prior Publication Data
US 2003/0096426 A1 May 22, 2003

Related U.S. Application Data

(62) Division of application No. 08/786,988, filed on Jan. 23, 1997.

(51) Int. Cl.
*G01N 24/00* (2006.01)
*G01N 1/10* (2006.01)
*B01D 59/44* (2006.01)

(52) U.S. Cl. .............. 436/173; 436/180; 250/287; 250/425

(58) Field of Classification Search .............. 250/288, 250/423 R, 442.11; 436/47, 173, 18; 422/104
See application file for complete search history.

(56) References Cited

U.S. PATENT DOCUMENTS

| | | | |
|---|---|---|---|
| 3,776,700 A | 12/1973 | Gallant | 23/259 |
| 4,740,692 A | 4/1988 | Yamamoto et al. | 250/282 |
| 4,952,518 A | 8/1990 | Johnson et al. | 436/518 |
| 5,175,209 A | 12/1992 | Beattie et al. | 525/54.11 |

(Continued)

FOREIGN PATENT DOCUMENTS

| | | |
|---|---|---|
| DE | WO-9803257 A * | 1/1998 |
| DE | 19731479 | 8/1998 |
| EP | 0396116 | 11/1990 |

(Continued)

OTHER PUBLICATIONS

Li et al. "Analysis of Single Mammalian Cell Lysates by Mass Spectrometry", J. Am. Chem. Soc., 1996, 118, pp. 11662-11663.
Beattie et al., "Synthesis and use of oligonucleotide libraries", *Chem. Abst.*, 123:1172 (1995).
Lyttle et al., "Versatile Linker Chemistry for Synthesis of 3'-Modified DNA", *Chem. Abst.*, 128(18):314 (1997).

(Continued)

*Primary Examiner*—Yelena G. Gakh
(74) *Attorney, Agent, or Firm*—Grant Anderson LLP

(57) ABSTRACT

Methods for dispensing tools that can be employed to generate multi-element arrays of sample material on a substrate surface. The resulting substrates are also provided. The substrates surfaces can be flat or geometrically altered to include wells of receiving material. The tool can dispense a spot of fluid to a substrate surface by spraying the fluid from the pin, contacting the substrate surface or forming a drop that touches against the substrate surface. The tool can form an array of sample material by dispensing sample material in a series of steps, while moving the pin to different locations above the substrate surface to form the sample array. The prepared sample arrays are passed to a plate assembly that disposes the sample arrays for analysis by mass spectrometry. To this end, a mass spectrometer is provided that generates a set of spectra signals that are indicative of the composition of the sample material under analysis.

40 Claims, 9 Drawing Sheets